United States Patent [19]
Smith et al.

[11] Patent Number: 5,922,316
[45] Date of Patent: Jul. 13, 1999

[54] COMPOSITION FOR ENHANCING GRAIN YIELD AND PROTEIN YIELD OF LEGUMES GROWN UNDER ENVIRONMENTAL CONDITIONS THAT INHIBIT OR DELAY NODULATION THEREOF

[75] Inventors: Donald L. Smith, Ste-Anne de Bellevue; Feng Zhang, Kingston, both of Canada

[73] Assignee: McGill University, Montreal, Canada

[21] Appl. No.: 08/668,468

[22] Filed: Jun. 25, 1996

[51] Int. Cl.$^6$ .............................. A01N 63/00; A01C 1/06; A01B 79/00
[52] U.S. Cl. .............................. 424/93.3; 47/57.6; 47/58; 47/DIG. 10; 435/252.2
[58] Field of Search ........................ 435/252.2; 424/93.3; 47/57.6, 58, DIG. 10

[56] References Cited

U.S. PATENT DOCUMENTS

| | | |
|---|---|---|
| 4,878,936 | 11/1989 | Handelsman et al. . |
| 5,141,745 | 8/1992 | Rolfe et al. . |
| 5,175,149 | 12/1992 | Stacey et al. . |
| 5,229,113 | 7/1993 | Kosslak et al. . |
| 5,321,011 | 6/1994 | Stacey et al. . |
| 5,432,079 | 7/1995 | Johansen et al. . |
| 5,484,718 | 1/1996 | Schofield et al. . |

FOREIGN PATENT DOCUMENTS

WO 94/25568  11/1994  WIPO .

OTHER PUBLICATIONS

Santibanez et al., "Genistein inhibits proliferation and in vitro invasive potential of human prostatic cancer cell line", Anticancer Res. 17 (2A) 1199–1204 (1997).

Lafavre et al., "Effects of high temperatures and starter nitrogen on the growth and nodulation of soybean", Crop Sci. 27(4): 742–745 (1987).

Kosslak et al., "Induction of Bradyrhizobium–japonicum Common NOD Genes by Isoflavones Isolated from Gycine–max", Proc. Natl. Acad. Sci. USA 84 (21): 7428–32 (1987).

Lynch, D.H. et al., 1993, Plant and Soil 157:289–303.

Zhang, Feng et al., 1994, Journal of Experimental Botany, vol. 45, No. 279, pp. 1467–1473.

Zhang, Feng et al., 1995, Environmental and Experimental Biology, vol. 35, No. 3, pp. 279–285.

Lynch, D.H., et al., 1994, Physiologia Plantarum 90:105–113.

Legros, T., et al., 1994, Environmental and Experimental Biology, vol. 34, No. 2, pp. 117–127.

Zhang, Feng et al., 1995, Plant Physiol. 108:961–968.

Primary Examiner—Sandra E. Saucier

[57] ABSTRACT

Compositions for enhancing grain yield and protein yield of a legume grown under environmental conditions that inhibit or delay nodulation thereof are provided. The compositions comprise a nodulation gene-inducing compound such as flavors. Moreover, methods for enhancing grain yield and protein yield of a legume grown under environmental conditions that inhibit or delay nodulation thereof are provided. The methods comprise an addition of an agriculturally effective amount of a nodulation gene-inducing compound such as flavors, in the vicinity of the seed or root of the legume. In particular, a condition which inhibits root nodulation is a root zone temperature below 25° C.

43 Claims, 3 Drawing Sheets

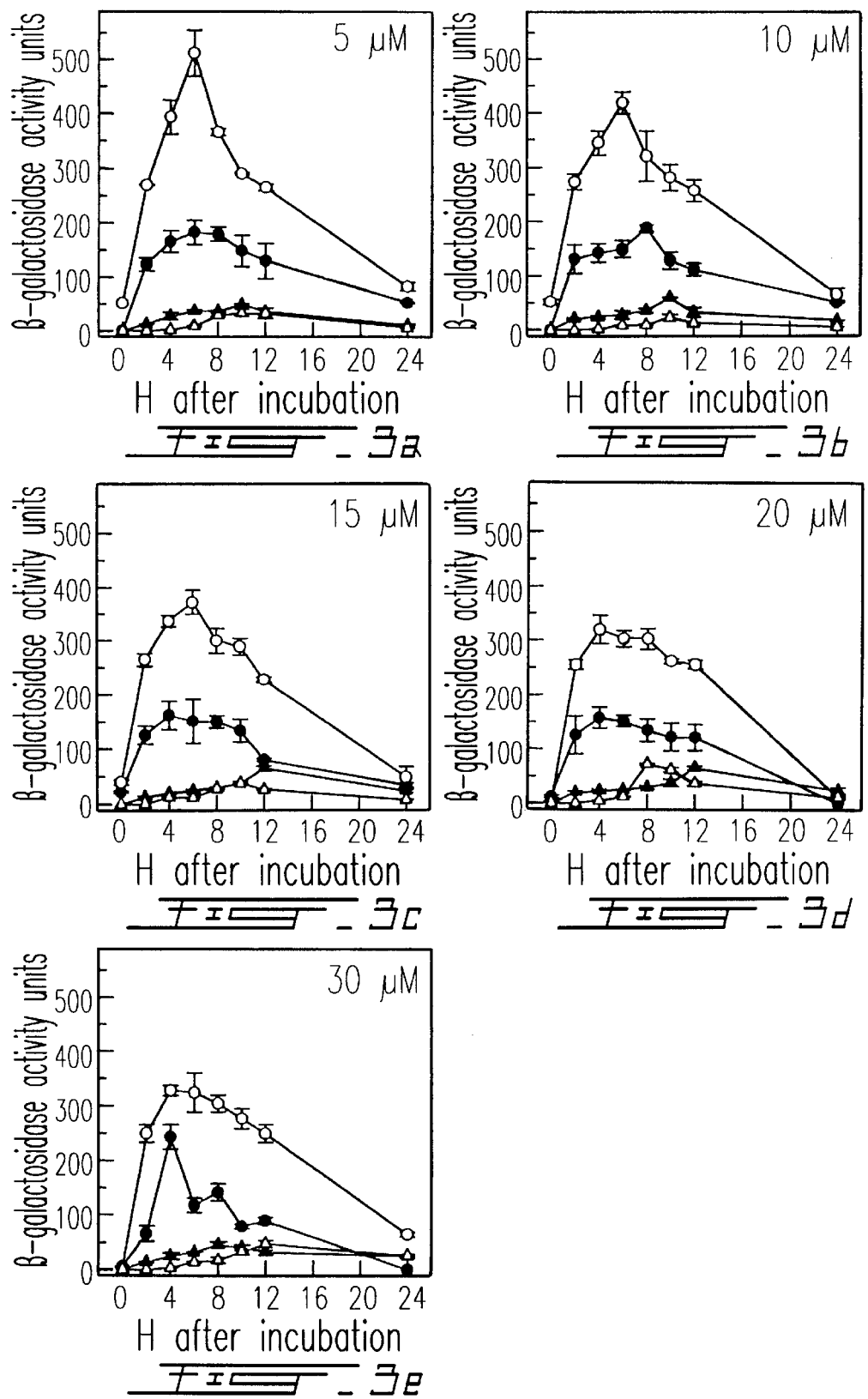

COMPOSITION FOR ENHANCING GRAIN YIELD AND PROTEIN YIELD OF LEGUMES GROWN UNDER ENVIRONMENTAL CONDITIONS THAT INHIBIT OR DELAY NODULATION THEREOF

FIELD OF THE INVENTION

The present invention relates to compositions and methods therefore for enhancing the formation and development of root nodules in legumes, so as to enable an increase in the growth and yield thereof under conditions that inhibit or delay nodulation. More particularly, the invention relates to compositions and methods therefore for increasing grain yield and protein yield of soybean grown under environmental conditions that inhibit or delay nodulation, such as suboptimal root zone temperatures (RATS).

BACKGROUND OF THE INVENTION

The knowledge that elements in the soil influence root nodulation has long been recognized. Indeed, the Romans transferred soil from successful legume fields to unsuccessful ones in order to improve the quality of the latter.

It has since then been demonstrated that one important soil element responsible for nodulation is soil bacteria. The family Rhizobiaceae consists of a heterogeneous group of gram-negative, aerobic, non-spore-forming rods that can invade and induce a highly differentiated structure, the nodule (on the roots, and in some instances, stems of leguminous plants), within which atmospheric nitrogen is reduced to ammonia by the bacteria. The family Rhizobiaceae contains three genera, Rhizobium, Bradythizobium, and Azorhizobium. The host plant is most often of the family Leguminosae. The slow-growing nodulation bacteria which have specific associations with soybean are referred to as Bradyrizobium. Currently, Bradyrhizobium has only one named species *B. japonicum*, with others lumped together in a miscellaneous group (Barbour et al., 1992); these latter strains are reformed to as B. sp., followed by the plant species they infect in parenthesis. Some soybean plants can also nodulate with the fast growing *Rhizobium fredii* (Sprent and Sprent, 1990). Rhizobium species, sometimes designated "fast-growing" rhizobia, include among others *R. meliloti* which infects alfalfa.

The element N is essential to all living organisms because it is a component of many biologically important molecules. The most important of these include nucleic acids, amino acids and therefore proteins, and porphyrins, which occur in large amounts in all living cells. To be able to multiply and grow, or just survive, organisms require a source of N. The ability to reduce atmospheric dinitrogen is limited to prokaryotes. Legumes and a few other plant species have the ability to fix atmospheric N through symbiotic relationships. In the case of legumes $N_2$-fixation is carried out by prokaryotes, Rhizobium or Bradyrhizobium in nodules located on the plant root (Sprent and Sprent, 1990).

Nodulation and the development of effective symbiosis is a complex process requiring both bacterial and plant genes. The molecular mechanisms of recognition between (Brady) rhizobium and legumes can be considered as a form of cell-to-cell interorganismal communication. A precise exchange of molecular signals between the host plant and rhizobia over space and time is essential to the development of effective root nodules. The first apparent exchange of signals involves the secretion of phenolic compounds, flavonoids and isoflavonoids, by host plants (Peters and Verma, 1990). These signal compounds are often excreted by the portion of the root with emerging root hairs, a region that is most susceptible to infection by rhizobia (Verma, 1992). These compounds have been shown to activate the expression of nod genes in rhizobia, stimulating production of the bacterial nod factor (Kondorosi, 1992). This nod factor has been identified as a lipo-oligosaccharide (Carlson et al., 1993), able to induce many of the early events in nodule development, including deformation and curling of plant root hairs, the initiation of cortical cell division, and induction of root nodule meristems. In soybean for example, the isoflavones, daidzein and genistein, are the major components of soybean root exudates which induce the nod genes of *B. japonicum* (Kosstak et al., 1987). Other such substances active at very low concentrations ($10^{-6}$ to $10^{-7}$M) have been shown to stimulate bacterial nod gene expression within minutes. However, the effectiveness of isoflavonoids is found to vary between cultivars.

The "common" nod genes, designated nodA, B and C, which are associated with the early stages of infection and nodulation, are structurally conserved among Rhizobium strains. In *R. meliloti, R. leguminosarum*, and *R. trifolii*, the nodA, B and C genes are organized in a similar manner and are believed to be coordinately transcribed as a single genetic operon. The DNA region adjacent and 5' to nodA has been found to contain a fourth nodulation gene, designated nodD, which is transcribed divergently from the nodABC operon. NodD has been found to function in the regulation of expression of nodABC and other nodulation genes.

Comparisons of the DNA sequences and the deduced amino acid sequences of the encoded nodD product confirm the presence of significant sequence conservation of these genes among strains of Rhizobium. nodD mutants in the various species of Rhizobium do not, however, display the same nodulation phenotypes. It now appears that many species of Rhizobium carry multiple nodD-like genes, on their Sym plasmids.

Another similarity in the nod region(s) of Rhizobium strains is the presence of conserved sequence elements within the promoter regions of certain inducible nod genes. These conserved sequences, first identified in the nodABC promoter region, are termed the nod-box and are believed to function in induced nod gene expression, possibly as regulatory protein binding sites.

No Sym plasmids have been associated with Bradyrhizobium strains. The nitrogenase and nodulation genes of these bacteria are encoded on the chromosome. Of importance, Bradyrhizobium strains contain nodulation genes which are reported to functionally complement mutations in Rhizobium and which show significant structural homology to nodulation gene regions of *R. meliloti* and *R. leguminosarum*.

In *Bradyrhizobium japonicum* strains USDA 110 and 123, nodABC and D gene structural homologs have been identified which are organized in a manner similar to their homologs in Rhizobium strains. NodD is read divergently from nodAB and C which are organized in a single operon. The untranscribed region between nodD and nodA also contains a copy of the conserved nod-box.

In contrast to Rhizobium strains, *Bradyrhizobium japonicum* strains contain another open reading frame, designated cum ORF, between nodD and nodA which is believed to be part of the nodABC operon.

The specific components of legume exudate that act to induce nodulation genes in several species of Rhizobium and Bradyrhizobium have been identified as flavonoids. Luteolin was reported to be the component of alfalfa exudates that induces nodABC expression in R. meliloti. Three clover exudate constituents: 4',7-dihydroxyflavone, geraldone and 4'-hydroxy-7-methoxyflavone were reported to induce the nodulation genes of R. trifolii. Two pea exudate components: eriodictyol, and apigenin-7-O-glucoside were reported to induce the nodulation genes of R. leguminosarum. In addition, molecules having structures related to those of the inducer found in exudate were assessed for their ability to induce. Inducers of Rhizobium nodulation genes appear in general to be limited to certain substituted flavonoids, and the range of compounds to which a Rhizobium responds is species specific. Since host range is used to classify Rhizobium strains into different species, this suggests that differential response to inducer molecules is involved in the mechanism of determination of host range.

Two isoflavone components of soybean exudate, daidzein and genistein, have been reported to be inducers of the nodulation genes of B. japonicum strains 110 and 123 (KosslaK et al. (1987) Proc. Natl. Acad. Sci. USA 84:7423–7432). Several other isoflavones were found to be inducers (7-hydroxyisoflavone, 5,7-dihydroxyisoflavone and biochanin A) or weak inducers (formononetin and prunetin) of the B. japonicum nod genes. In addition, two flavones: 4',7-dihydroxyflavone and apigenin which induce certain Rhizobium nod genes were also found to induce the B. japonicum nod genes.

In view of the above, it is clear that the exchange of signals between legume and bacterial strain and intricacies thereof are shared between different legumes and the Rhizobium and Bradyrhizobium generas.

The manner in which nodulation genes are regulated is also conserved among Rhizobium and Bradyrhizobium strains.

Soybean [Glycine max (L.) Merr.] is the world's most widely-produced nitrogen (N) fixing crop. However, soybean is a plant of tropical to subtropical origin and, as such, requires temperatures in the 25 to 30° C. range for optimal growth and symbiotic $N_2$ fixation. When well-nodulated, soybean is capable of fixing its own N. Both symbiotic $N_2$ fixation and $NO_3$-utilization appear to be essential for maximum yield. High soybean yields also require adequate levels of phosphorous and potassium. Liming acid soils to a pH of 6.0 to 6.5 is an important prerequisite for profitable soybean production. Adequate populations of Bradyrhizobium japonicum must be present to produce a well-nodulated soybean crop. Smith et al. (1981) determined that an inoculum level above $1 \times 10^5$ rhizobia per centimetre of row was necessary to establish effective nodulation.

Root zone temperatures (RZTs) below 25° C. strongly and negatively affect soybean nodulation and $N_2$ fixation (Lynch and Smith, 1994). In fact, in short season areas low temperature is considered the major growth limiting factor for soybean. It has been noted that all stages of nodule formation and functioning are affected by suboptimal RZTs and experiments have generally indicated that early nodule development processes are the most sensitive. The exact mechanism by which suboptimal RZTs affect N fixation has yet to be identified. Numerous hypothesis have been postulated however: 1) decrease N fixation activity by the nitrogenase enzyme complex; 2) changes in nodule oxygen permeability; 3) rate of export of fixed N from the nodule; 4) inhibition of $N_2$ fixation inside the nodule; 5) decrease in bacteroid tissue and/or delay in its rate of formation; 6) via effects on bacterial physiology and growth; and 7) via effects on plant physiology and growth.

Production or N fertilizer, in Canada as elsewhere, is economically ($1 billion per year in Canada), energetically (equivalent to 30 million barrels of oil per year) and environmentally (produce 15 million tones of $CO_2$ per year, ground water-polluting $NO_3$ and ozone-destroying $NO_x$) expensive. In eastern Canada the farm community spends approximately $150 \times 10^6$ per year for N fertilizer. Nitrogen fixation is the sustainable alternative to N fertilizer. Therefore, an understanding of the mechanism of suboptimal RZT effects on soybean nodulation and $N_2$ fixation and finding methods to reduce this restriction by low RZT would allow increased use of this $N_2$-fixing cash crop, and decreased reliance on potentially polluting N fertilizers in cool season areas. The ability to overcome the negative effects of suboptimal RZTs could be applied to other conditions that negatively affect nitrogen fixation (water stress, high pH, temperatures etc.).

Due to the number of benefits which can result from the establishment of rhizobia:legume symbiosis, a number of strategies have been devised to promote nodulation of legumes.

U.S. Pat. No. 4,878,936 to Handelsman et al., teaches a method for enhancing nodulation of legumes which includes inoculation in the immediate vicinity of the roots thereof, an effective quantity of bacteria which enhance nodulation. However, the results are based on controlled laboratory conditions, not on field studies. Moreover, the laboratory conditions used, involved temperatures above 25° C. which are not expected to be limiting for nodulation.

U.S. Pat. No. 5,141,745 to Rolfe et al., discloses flavones, some of which are leguminous plant exudates, which induce expression of certain nod genes in rhizobium strains. Rolfe et al., however, do not assess whether their results, all obtained under laboratory conditions, translate into increase nodulation and growth of the leguminous plant under field conditions.

The art is replete with examples demonstrating that results obtained under the laboratory setting are not predictive of the field situation. Typically, a good controlled environment provides optimal levels of soil nutrients, soil pH, soil moisture, air humidity, temperature and light. The plants are usually widely spaced so that they do not compete for light and the light intensity is usually high. In some cases environmental factors such as carbon dioxide may even be optimized. The field environment is vastly more complicated than that of the controlled environment setting. The soil will vary in its chemistry and texture in a fractal pattern, such that, while the soil of a research site can be characterized in general, it will be variable at every level within the confines of the experimental area. In a controlled environment setting plants are usually produced in sterilized rooting media (pasteurized soil, sterile sand, or some form of artificial rooting media) and there is no soil micro flora or fauna. Field soil is an ecosystem; it contains an enormous number of bacteria, fungi, protista, algae, and soil insects. The climate and related atmospheric factors (light intensity, relative humidity, temperature, rainfall, carbon dioxide concentration of the air, presence of pollutants) vary constantly under unpredictably field conditions. Thus, a researcher may impose a nutrient limitation in the field, but if the conditions are dry and water is more limiting to plant growth than the nutrient in question, there will be no discernable effect due to nutrient treatments.

The inability to extrapolate from a laboratory to a field setting is illustrated by work conducted in the 1970's and early 1980's on soybean with strains of Bradyrhizobium japonicum which were hypothesized to be more energy efficient when fixing nitrogen. Because of the extreme stability of the triple bond in the dinitrogen molecule nitrogen fixation was known to be a very energy expensive process (reviewed In Schubert 1982). In addition, it was discovered that the enzyme which fixed dinitrogen into biologically useful ammonia (nitrogenase) leaked high energy electrons to protons, so that every time one dinitrogen molecule was fixed into two ammonia molecules, at least one dihydrogen (the product of two protons plus two electrons) was produced. This constituted a waste of energy by the plant-bacterium symbiotic system. Shortly afterward it was discovered that some strains of B. japonicum contained an enzyme that took up the hydrogen formed and took the high energy electrons back off the protons, hence recovering much of the energy that would have been lost (Schubert et al, 1978). This lead to speculation that strains containing these "uptake hydrogenases", referred to as Hup+ strains, would be more efficient and lead to improved plant growth, as the plant would have to supply less energy (as organic acids) to the bacteria for each ammonia molecule received from them. Albrecht et al. (1979) compared soybean plants inoculated with Hup+ and Hup− strains of B. japonicum under greenhouse conditions. Average total nitrogen contents and total dry weights of Hup+ inoculated plants were shown to be larger than those of plants inoculated with Hup− strains. This was confirmed by Maier et al. (1978). However, under field conditions, Albrecht et al. (1979) were unable to detect an increase in dry matter production or yield between Hup+ and Hup− strains. These results were confirmed by numerous field condition studies. During the course of these confirmations however, a superior strain of B. japonicum (532c), which is now included in almost all soybean inoculants used to produce soybean in Canada, was identified (Hume et al., 1990). Strikingly, this strain is Hup−.

This example provides a blatant proof involving soybean, that results obtained in a controlled milieu are a priori not predictive of the field situation.

U.S. Pat. No. 5,175,149 of Stacey et al., teaches that the mere coating of the leguminous seeds or sowing of the soil with the desired bacterial strins does not necessarily lead to the desired inoculation of the plant. Therefore, they provide a means for inducing nodulation on the roots of leguminous plants that is independent of the presence of rhizobial bacteria, by using the bacterial signal molecule directly (lipo-oligosaccharide), thereby by-passing the plant signal molecule (flavonoids).

U.S. Pat. No. 5,229,113 ('113) issued to Kosslak et al., relates to nodulation-inducing compositions and methods of selectively activating nod genes under the control of a soybean exudate inducible promoter responsive to inducer molecules. Similarly to U.S. Pat. No. 5,141,745, '113 does not teach or suggest that their compositions and methods are operational under field conditions and/or under conditions that inhibit or delay nodulation.

PCT patent application WO 94/25568, which was published Nov. 10, 1994 in the name of Rice et al., discloses cold tolerant strains of Rhizobium which are useful for improving nodulation, nitrogen fixation and overall crop size under field conditions. However, it is unclear whether the cold-selected strains indeed provided an advantage to Alfalfa, since in certain experiments the temperate strains performed better than the cold-temperature selected strain (i.e. Tables 5,6 and 7). This results corroborates the findings of Lynch et al., 1994 which suggested that inoculation with B. Japonicum strains from cold environments is unlikely to enhance soybean N2-fixation under cool soil conditions. Lynch et al., 1994 also suggested that indeed the host plant, and not the bacterial strain, mediates at least a significant portion of the sensitivity of N2-fixation under low RZT. Further WO 94/25568 (see below) teaches that commercial rhizobial inoculants are not consistent in their efficacity and performance, and nodulation failures after use of commercial inoculants are common. This is explained by the inability of inoculant strains to out-compete indegenous rhizobial bacteria for root-infection sites, once again demonstrating the non-predictivity of lab results to the field conditions. In any event WO 94/25568 fails to provide any teaching or suggestion as to involvement of the signal molecules in the initiation of the nodulation event and their effect under field conditions.

U.S. Pat. No. 5,432,079 to Johansen et al., relates to the isolation of Rhizobium strains having improved symbiotic properties. Once again this Patent falls to teach an enahancement of growth and or yield of a legume under field conditions. Moreover, this document is silent on the use of flavonoids or the like to achieve that goal. It teaches however that a higher expression of the nod genes does not necessarily provide an advantage, but can be detrimental to the competitive ability of the Rhizobium strains.

To date there has been no investigation as to whether nodulation inbiting or delaying factors, such as suboptimal RZTs alter plant to bacteria signaling.

An understanding of the mechanism of suboptimal RZT effects on soybean nodulation and $N_2$ fixation and finding methods to reduce this restriction by low RZT would allow increased use of this $N_2$-fixing cash crop, and decreased reliance on potentially polluting N fertilizers in cool season areas. Elucidation of the mechanism for suboptimal RZTs effects on nodulation and nodule formation in soybean and a determination of how to reduce the negative effect of suboptimal RZTs on the soybean. $N_2$ fixation symbiosis under the cool spring conditions or other conditions which inhibit or delay this symbiosis would provide a significant advantage to the production of legumes. For example, it would be advantageous to understand whether the poor nodulation of soybean at suboptimal RZTs are related to the plant's ability to synthesize and/or excrete plant-to-bacterial signal molecules.

There thus remains a need to reduce the the negative effects of environmental factors on nodulation and nodule formation and to provide compositions and methods to enable the enhancement of grain yield and protein yield of legumes grown under environmental conditions that inhibit or delay nodulation thereof.

The description found hereinbelow refers to a number of documents, the content of which is herein incorporated by reference.

Recent reviews on nodulation factors and Rhizobium symbiosis are available: Spaink, 1995, "Molecular basis of injection and nodulation by Rhyzobia—the ins- and outs of sympathogenesis". Ann. Rev. Phytopathol. 33:345–368; and Prome et al., 1996, "Nodulation factors in plant microbe interactions, Ed. Stacey et al., Pub. Chapman and Hall.

SUMMARY OF THE INVENTION

The Applicant was the first to demonstrated that between 25 and 17° C. RZTs, the onset of N2 fixation was delayed by 2.5 days for each degree decrease in temperature, while below 17° C. each ° C. appeared to delay the onset of N2 fixation by about 7 days. Since growing plants at 19 instead of at 21° C. for only a few days can make an important difference in the time to onset of $N_2$ fixation, the Applicant emphasized that infection and/or early nodule development were the stages most sensitive to low RZT (Zhang et al., 1995a).

The Applicant having identified that an early stage in the complex process leading to nitrogen fixation was affected, it was hypothesized that the poor nodulation observed at suboptimal RZT was related to a disruption of plant-to-bacteria signalling during initiation of the symbiosis. *B. japonicum* cells were thus preincubated with genistein, a major isoflavonoid signal molecule in soybean plants prior to addition to soybean root systems. Before these experiments and their publication (Zhang et al., 1995b) there had been no investigations as to whether an inhibitor of the early steps of nodulation, such as suboptimal RZTs altered plant-to-bacteria signaling. Moreover, there had been no investigation that an environmental variable adversably affected nodulation of a legume through disruption of interorganismal signal exchange. The applicant is thus the first to provide data showing that the inhibition of soybean nodulation at suboptimal RZTs is due to a disruption of plant-to-bacterial signal exchange. Furthermore, the Applicant has determined, under controlled conditions, that preincubation of *B. japonicum* with genistein increased soybean nodulation and nitrogen fixation under suboptimal RZT conditions, and that with decreasing temperature, a higher genistein concentration is required.

Following their demonstration that preincubation of *B. japonicum* with genistein increased soybean nodulation and nitrogen fixation at three RZTs under controlled environment conditions, the Applicant then showed that this technique, together with genistein directly applied into the plant rhizosphere, accelerates the onset of soybean nitrogen fixation and increases total seasonal fixed nitrogen under field conditions in a short season area (Zhang et al., 1991c). Moreover, the Applicant further showed that incubation of *B. Japonicum* with genistein prior to application as an inoculant, or geneistein, without *B. Japonicum*, applied onto seeds in the furrow at the time of planting, increased soybean nodulation, N fixation and total N yield, under field conditions which delay or inhibit nodulation (Zhang et al., 1996). The results of these experiments further indicated that genistein application increased nodule number and nodule dry matter per plant and hastened the onset of nitrogen fixation during the early portion of the soybean growing season, when the soils were still cool (conditions that delay or inhibit nodulation and nitrogen fixation). Because these variables were improved, total fixed N. fixed N as a percentage of total plant N, and N yield increased due to genistein application. In addition, the results indicated that genistein application was more effective on N-stressed plants.

Before the above-mentioned results from the Applicant, there had been no prior investigations of whether preincubation of *B. japonicum* with genistein increases soybean nodulation and $N_2$ fixation under field conditions, where other factors such as greater $CO_2$ limitation, or the complex nature of the soil microflora may alter the effects observed indoors.

Thus in a first aspect, the present invention features compositions for enhancing protein yield and grain yield of legumes grown under environmental condition which inhibit or delay nodulation thereof.

In a related aspect, the invention features methods for enhancing protein yield and grain yield of legumes grown under environmental condition which inhibit or delay nodulation thereof.

In one preferred embodiment, the present invention features compositions end methods for enhancing protein yield and grain yield of soybean grown under environmental condition which inhibit or delay nodulation thereof.

Further broad aspects of the instant invention include a method of increasing the growth and/or of protein yield and/or of seed yield of legume crops grown under environmental conditions which inhibit or delay nodulation thereof with an agriculturally effective amount of a composition comprising a Rhizobial strain in admixture with a flavonoid nodulation gene inducing compound and an inoculant carrier medium.

In accordance with the present invention, there is provided a composition for enhancing grain yield and protein yield of a legume grown under environmental conditions that inhibit or delay nodulation thereof, the composition comprising an agriculturally effective amount of a nodulation gene-inducing compound in admixture with a suitable carrier medium.

In accordance with the present invention, there is also provided a method for enhancing grain yield and protein yield of a legume grown under environmental conditions that inhibit or delay nodulation thereof, comprising:
a) incubating a rhizobial strain which nodulates said legume with an agriculturally effective amount of a nodulation gene-inducing compound; and
b) inoculating in the vicinity of one of a seed and root of said legume with said rhizobial strain of a).

While the instant invention is demonstrated by experiments performed with *Bradyrhizobium japonicum* and soybean, the invention is not so limited. Other legume crops, and rhizobial strains may be used using the same principle taught herein. Non-limiting examples include, alfalfa, *Rhizobium meliloti* and a nod gene inducing factor thereof; clover *R. meliloti*, and a nod gene inducing factor thereof; clover *R. trifolli*, and a nod gene inducing factor thereof; *R. leguminosarum* peas or lentils, and a nod gene inducing factor thereof; and beans *R. phaesoli* and a nod gene inducing factor thereof. Preferred matching of Rhizobium species with legume crop groups include:

| Rhizobium species | Legume crop group |
|---|---|
| R. melilotti | alfalfa, sweet clover |
| R. leguminosarum | peas, lentils |
| R. phaesolii | beans |
| Bradyrhizobium japonicum | soybeans |
| R. trifolii | red clover |

While the instant invention is demonstrated by experiments performed using genistein or daidzein as preferred nodulation inducing compounds, the invention is not so limited. U.S. Pat. No. 5,141,745 teaches the molecular structural features that are associated with nodulation inducing activity of plant exhibits. Therein, a number of flavonoids, isoflavonoids, flavones including flavanones, flavanols and dihydroflavanols, isoflavones, coumarins and related molecules were assayed for noduliaon inducing activity. Nodulation inducing activity was found to reside in a structurally identifiable group of compounds not limited to those flavones associated In particular with legumes which include specifically substituted flavones, flavonones (dihydroflavones), flovanols (3-hydroxyflavones) and dihydroflavanols. The basic flavone ring structure common to flavones, flavonones, flavanols and dihydroflavanols is requisite for activity. Within the group of flavones, it is clear that substitution at the 7th position with a hydroxyl group leads to a strong stimulatory activity. It is also clear that substitution of hydroxyl or methoxyl moieties at positions 5, 3, 2' or 4' in addition to 7-hydroxyl substitution does not abolish activity. Nor, in general, does substitution of hydroxyl or methoxyl moieties at position 3' in addition to 7-hydroxyl substitution abolish activity.

However, flavones or dihydroflavones substituted with either hydroxyl or methoxyl at both the 3' and 4' positions require in addition to 7-hydroxylafion a hydroxyl group at the 5 position for activity. The fact that rutin, a 3-O-glycoside of the flavone quercetin, is active for nodulation gene induction not only indicates that quercetin is active but also that 3-O-glycoside substitution does not abolish inducing activity. In contrast, substitution of a glucoside at the 7 position is believed to abolish activity. Replacement of the 7-hydroxy group with a methoxy group decreases but does not abolish stimulatory activity as evidenced by the weak activity of 4'-hydroxy-7-methoxyflavone. By analogy to active 7-hydoxyl substituted flavones, 5-hydroxy-7-methoxyflavone, 4',5'-dihydroxy-7-methoxyflavone and 3,4',5'-trihydroxy-7-methoxyflavone and tehir dihydroflavone analogs are expected to have stimulatory activity, albeit weak. The fact that taxifolin and naringein, both flavanones, have stimulatory activity indicates that the double bond in the flavone fused ring (between positions 2 and 3) Is not necessary for nodulation gene-inducing activity. This implies that all flavones and dihydroflavanols having substitution patterns as described above have nodulation inducing activity. Although alkoxy substituted flavone other than methoxy have not been identified from natural sources, there is no reason to believe that alternative short chain substituents like ethoxy or propoxy groups would abolish nodulation gene induction activity.

As exemplified in the present application, synthetic as well as natural nodulation gene-inducing compounds are encompassed by the scope of the present invention.

Direct or indirect methods of legume inoculation can be employed. During direct inoculation the bacterium is applied directly to the seed prior to sowing. This can most simply be accomplished by spraying the seed with or dipping the seed into a liquid culture containing a desired Rhizobium strain and a nodulation gene inducer. A preferred method of direct inoculation is pelleting of the seed with an inoculating composition containing a Rhizobium strain and a nodulation gene-inducing factor. Generally, the bacterium is applied to a carrier material and a pellet is formed with the carrier surrounding the seed. Many diverse carriers are known in the art and include, among others, peat, soil, calcium carbonate, dolomite, gypsum, clay minerals, phosphates, titanium dioxide, humus and activated charcoal. Any agriculturally suitable material can be employed. An adhesive material is often included in such a pellet to insure that the carrier remains in contact with the seed. Again, many acceptable adhesives are known including, among others, synthetic glues, vegetable glues, gelatin and sugars. In general, the carrier and any adhesive used are chosen to insure viability of the inoculant strain and retention of activity of nodulation gene-inducing factor. Pelleted inoculated seed containing an inducing factor can be directly sown into the field. Alternatively, a conventionally prepared inoculated seed or seed pellet containing the desired strain can be contacted with an inducing composition containing an effective amount of a nodulation gene inducer before, with or after sowing of the inoculated seed.

The concentration of nod gene inducing compound will be adapted to the particular situation at hand by the skilled artisan. For example, the skilled artisan will take into account the level of severity of inhibition or delay of the environmental conditions on nodulation, the responsiveness of the nod genes of the rhizobial strain to the nod gene inducing compound, the method of application of the composition, etc. The upper limit of the effective concentration is determined by toxicity of the nod gene inducing compound toward the rhizobial strain or, if applicable, by the solubility limit of the inducer in the carrier chosen.

During indirect inoculation, an inoculating composition of the present invention containing an inoculant strain and an effective concentration of a nodulation gene inducer is introduced in the vicinity of the seed at the time of sowing.

Having now demonstrated that nodulation gene-inducing factors are effective under field conditions, another use of the present invention is for the selective induction in bacteria of genes containing a legume nodulation gene-inducing promoter in a structural gene under its control. Expression of this structural gene under the control of a nod gene-inducing promoter can be activated by the addition of the activator therefor. Having demonstrated that these promoters are affected by environmental factors such as temperature, the present invention provides a means to somehow regulate, through the field conditions, the level of expression of the structural gene under the control of the above-mentioned promoter. Construction of such chimeras can be adapted using conventional methods by the skilled artisan.

Hereinafter, the invention is illustrated with reference to *B. japonicum* and soybean, but is demonstrative of utility of the invention with other Rhizobium and Bradyrhizobium species and other legume crop groups. Indeed, herein the term rhizobla is used loosely and encompasses Rhizobium and Bradyrirzobium species.

The term "environmental conditions which inhibit or delay nodulation" should be interpreted herein as designating environmental conditions which postpone or inhibit nodulation and nitrogen fixation and include, without being limited thereto: conditions that stress the plant, such as temperature stress, water stress, pH stress as well as inhibitory soil nitrogen concentrations or fixed nitrogen.

As used herein, the term "enhancing protein yield and grain yield" refers to an enhancement of protein and grain yield of legumes of treated plants in accordance with the present invention or adaptations thereof as compared to control plants.

"An agriculturally effective amount of a composition" for increasing the growth of legume crops refers to a quantity which is sufficient to result in a statistically significant enhancement of growth and/or of protein yield and/or of grain yield of a legume crop as compared to the growth, protein yield and grain yield of a control crop.

The term "immediate vicinity of a seed or roots" refers to any location of a seed or roots wherein if any soluble material or composition is so placed, any exhibit of the plant or of the bacteria, or bacterial cells will be in actual contact with the seed as it germinates or the roots as they grow and develop.

By "nodulation gene-inducing" or "nod gene-inducing" is meant bacterial genes involved in nodule establishment and function.

Other objects, advantages and features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 3 shows the effect of temperature (($\Delta$) 10, ($\blacktriangle$) 15, ($\circ$) 25 and ($\bullet$) 30) on β-galactosidase activity of *B. japonicum* with a nodY-lacZ fusion over the first 24 h of incubation with 5 genistein concentrations. Genistein was tested for the ability to induce transcription of β-galactosidase from *B. japonicum* USDA110 harboring plasmid ZB977 (nodY-lacZ). The background level of β-galactosidase activity was substracted. Each value is plotted as the mean ±SE (n=4).

DESCRIPTION OF THE PREFERRED EMBODIMENT

Figure 1:
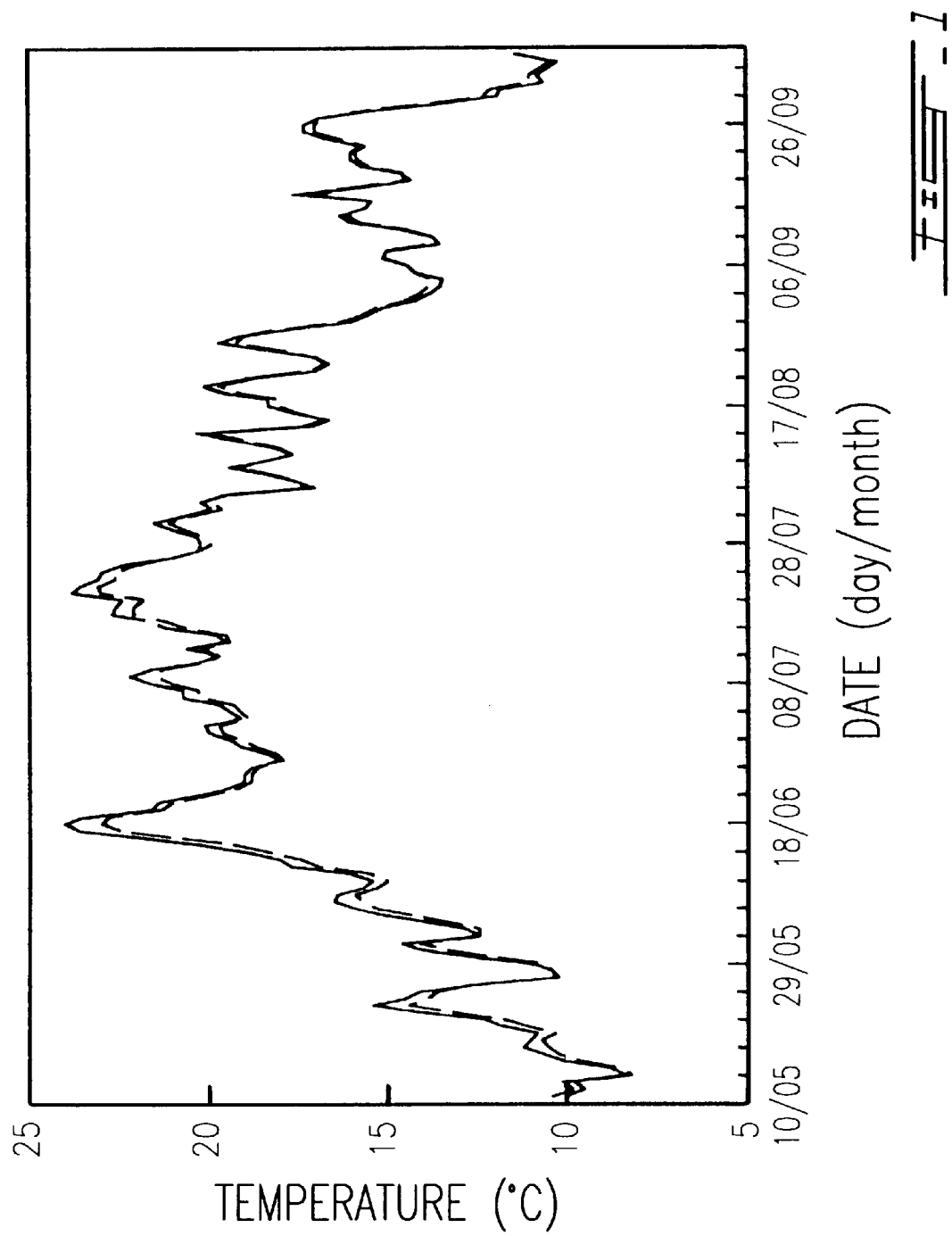
FIG. 1 shows the average daily soil temperature at depth of 5 (solid line) and 10 cm (dotted line) during the soybean growing season in 1994 (Ste Anne de Bellevue, Quebec, Canada)
Figure 2:
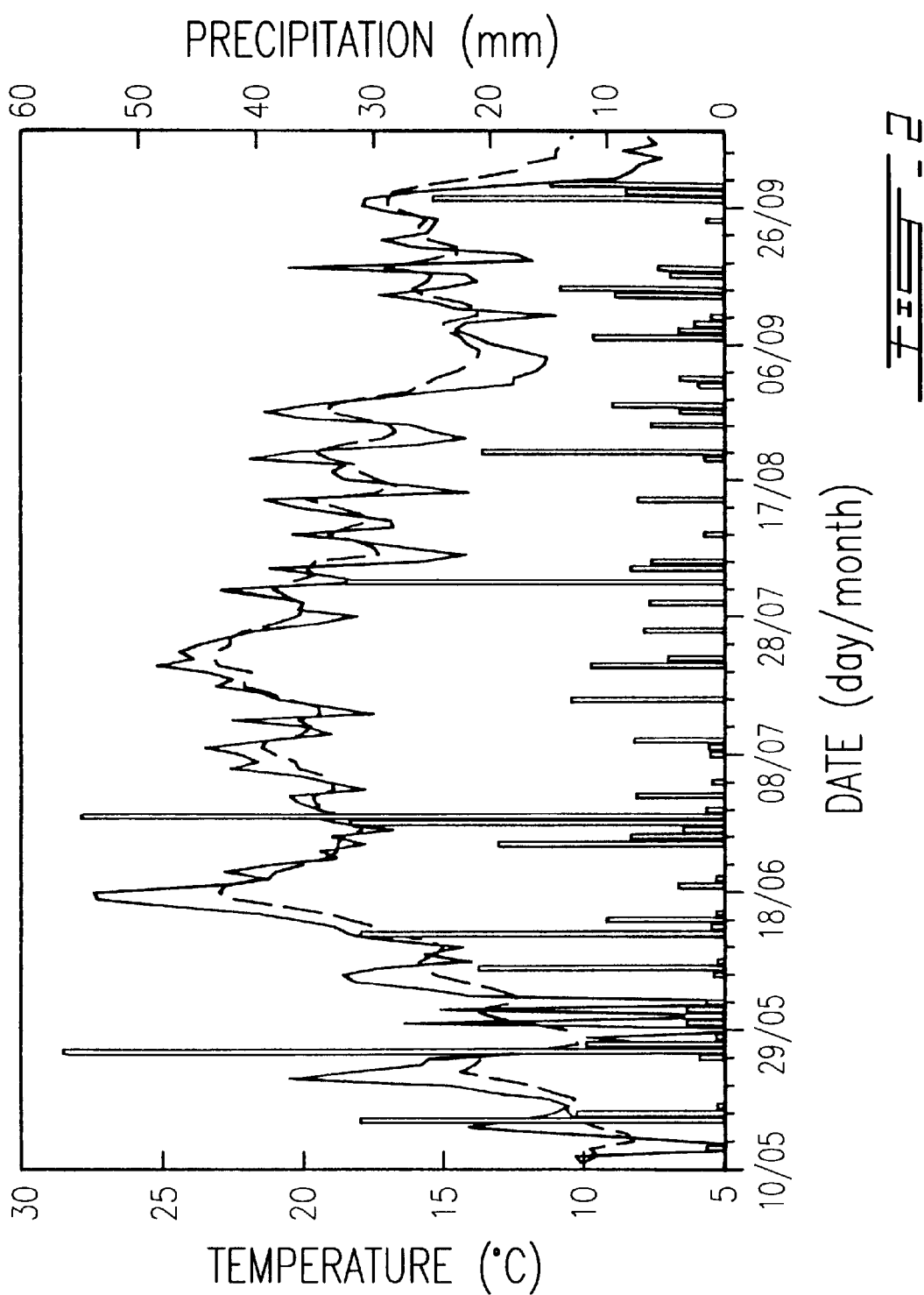
FIG. 2 shows the average daily temperatures of air (solid line) and soil at a depth of 5 cm (dashed line) and precipitation (bar) during the soybean growing season in 1994 (Ste Anne de Bellevue, Quebec, Canada)

PREINCUBATION OF *B. japonicum* WITH GENISTEIN ACCELERATES NODULE DEVELOPMENT OF SOYBEAN AT SUBOPTIMAL RZTs Controlled environment studies wre performed to determine the influence of an environment factor, such as RZT, on plant growth, nodulation and N fixation.

Plant Materials

Seed of the soybean [*Glycine max* (L.) Merr.] cv Maple Glen was surface-sterilized in sodium hypochlorite (2% solution containing 4 mL L$^{-1}$ Tween 20) and then rinsed several times with distilled water. This cultivar was selected because it was developed for production under the short season, cool conditions of eastern Canada and it has performed well there. The seeds were sown in trays containing a sterilized Turface (Applied Industrial Materials Corp., Deerfield, Ill.):sand (1:1, v/v) mixture. Seven-day-old seedlings at the VC stage [unifoliolate leaves unrolled sufficiently that the edges were not touching] were transplanted into sterilized 13 cm plastic pots containing the same medium and maintained in a growth chamber (model GB48, Controlled Environments Ltd., Winnipeg, Manitoba, Canada) at an irradiance of 300 $\mu$mol m$^{-2}$ s$^{-1}$ for a 16:8 hours (day:night) photoperiod and a constant air temperature of 25° C.

The pots were sealed to the bottom of plastic tanks (68×42 cm) and RZTs (±0.5° C.) were controlled by circulating cooled water around the pots, with eight pots in each tank. A hole drilled in the tank bottom below each pot allowed the pots to drain when watered. There were nine tanks in the growth chamber. Plants were then acclimatized for 24 hours prior to inoculation. Plants were watered with a modified Hoagland solution, in which the CaNO$_3$ and KNO$_3$ were replaced with 1 mM CaCl$_2$, 1 mM K$_2$HPO$_4$ and 1 mM KH$_2$PO$_4$, to provide a nitrogen-free solution. Prior to each watering, the added Hoagland solution was temperature adjusted to the treatment RZT.

Bacterial Materials

The inoculum was produced by culturing *Bradyrhizobium japonicum* strain 532C (Hume and Shelp, 1990) in yeast extract mannitol broth in 250 mL flasks shaken at 125 rpm at room temperature. Strain 532C has been shown to perform well over a range of temperatures (Lynch and Smith, 1993, Physiol. Plant 88:212–220). For production of *B. japonicum* preincubated with genistein, 10 mL of a cell suspension from a 3-day-old (log phase 2×10$^9$ cells mL$^{-1}$) sub-culture were aseptically added to 50 mL of sterile genistein solution in a 250 mL Erlenmeyer flask and incubated at 30° C. without shaking for 48 hours (Halverson and Stacey, 1984). Following incubation, the cell suspensions were pelleted in sterile centrifuge tubes at 7000 g for 10 minutes, washed once with distilled water, and resuspended to an A$_{620}$ of 0.08 (approximately 10$^5$ cells mL$^{-1}$). The inoculum was cooled to the corresponding root temperature and 1 mL of the inoculum was applied by pipette onto the rooting medium at the base of the plant.

EXPERIMENT 1

In this experiment, two forms of genistein (4',5,7-trihydroxyisoflavone) were tested: one isolated from soybean (purity of 98%) and one synthetic (purity of 98%). The two forms of genistein were obtained from Sigma. The experiment was arranged as a completely randomized split-plot design with three replications. RZTs were treated as main-plot units, at 25° C. [optimal temperature for soybean nodulation and N$_2$ fixation, 17.5° C. [suboptimal temperature but still above the critical 17° C., below which soybean nodulation and N$_2$ fixation were strongly inhibited (Lynch and Smith, 1993; Zhang et al., 1995a Environ. Experiment, Bot. 35: 279–285)], or 15° C. [at this RZT soybean nodulation was strongly inhibited (Lynch and Smith, 1993a)]. Each main-plot replication was one of the nine tanks described above. The sub-plot factor was genistein concentration at 5, 10, or 15 $\mu$M for the synthetic genistein or at 5, 10, 15, or 20 $\mu$M for the isolated genistein. No genistein (0 $\mu$M) application was used as a control. The synthetic genistein was tested at only three levels because each of the replicate tanks could accommodate only eight pots (experimental units). In this experiment. plants were harvested 50 days after inoculation (DAI) and the following data were collected: nodule number; nodule dry weight; specific nodule weight; plant nitrogen content (Kjeltec, Tecator A B, Hoganas, Sweden); and growth variables, such as leaf number, leaf area, shoot weight, and root weight. Fixed nitrogen per plant was calculated by the total plant nitrogen content minus the amount of nitrogen in the original seed (11.5 mg seed$^{-1}$; average of 25 seeds). Because the effects of the two forms of genistein were not different for any soybean nodulation variable, N$_2$ fixation, or growth, the synthetic genistein was chosen for experiments 2 and 3.

Typically, the leaves of inoculated soybean plants growing in a 0N medium initially changed from a healthy green to yellow because of depletion of seed nitrogen reserves. Two days after nitrogenase activity (acetylene reduction activity) was detected, the fully expanded uppermost leaves began to regain their colour and vigour, and at that point sharply increased their photosynthetic rate (Zhang et al., 1995a). Since the uppermost leaf regreening and photosynthetic rate were easily and non-destructively measured, these were used to indicate when the plants had started to fix N$_2$ (Zhang and Smith, 1994). Therefore, in this experiment, the photosynthetic rate of the central fully expanded uppermost leaflet was measured and was used to indicate the onset of N$_2$ fixation by plants exposed to different treatments. The photosynthetic measurements were taken by a LI-6200 portable photosynthesis system (Li-Cor Inc., Lincoln, Nebr.), between 2 and 6 PM.

EXPERIMENT 2

This experiment extended the range of genistein concentrations tested in an effort to determine the optimum level of synthetic genistein addition to *B. japonicum* cultures for stimulation of soybean nodulation at suboptimal RZT. This experiment followed the same design as experiment 1. Plants were harvested 50 DAI and the data collected were the same as in the first experiment.

EXPERIMENT 3

This experiment was conducted to determine whether or not the time required for the various Infection steps was shortened by genistein application. The treatments were arranged in a completely randomized factorial design with four replicates. The experiment had three temperature levels (25, 17.5, and 15° C.) and two synthetic genistein levels (0 and 20 $\mu$M) for a total of six treatments. Within each RZT, two plants were harvested each day from 1 until 10 DAI. Plant roots were washed in distilled water and the six uppermost secondary roots of each plant were taken for microscopic observation. Twelve roots were stained with 1% aniline blue for 10 min. Then six plant roots were taken randomly from the 12 roots that were harvested from two plants and observed under a light microscope (Jenalumar, Jena Instruments Ltd., Jena, Germany). The effects of genistein on the durations of the various morphological changes during the early soybean nodule infection stages, which were described over a range of RZTs by Zhang and Smith (1994 J. Exp. Bot. 279:1467–1473), were investigated at the three RZTs indicated.

Statistical Analysis

Results were analyzed statistically by analysis of variance using the Statistical Analysis System computer package (SAS Institute Inc., 1988). When analysis of variance showed significant treatment effects, the LSD test was applied to make comparisons among the means at the 0.05 level of significance.

Genistein Effects on Nogulation and Nodule Mass

At 25° C. RZT, nodule numbers of plants with 0 $\mu$M genistein application 50 DAI ranged from 97.0 to 107.2. When the RZT was 17.5 or 15° C., the number of nodules per plant was reduced to 59.3 or 48.3% of that at 25° C., respectively. The preincubation of B. japonicum with genistein at 25° C. RZT did not affect (p<0.05) nodule number in experiment 2. However, in experiment 1 pretreatment of B. japonicum with either synthetic or isolated genistein increased nodule numbers at 5 $\mu$M and decreased nodule numbers at higher concentrations. At 17.5 and 15° C., some concentrations of genistein were found to increase nodule number in both experiments 1 and 2. In experiment 1, the nodule numbers increased with increasing genistein concentrations, and the stimulation was still increasing at 15 $\mu$M for chemically synthesized genistein and 20 $\mu$M for genistein isolated from soybean plant. The effects of synthetic and isolated genistein followed the same pattern.

In experiment 2, synthetic genistein application above 20 $\mu$M either did not further increase (15° C.) or decreased (17.5° C.) nodule number. Nodule stimulation for plants grown at an RZT of 17.5° C. occurred over a somewhat lower synthetic genistein concentration range (10–20 $\mu$M) than for plants grown at 15° C. RZT (10–40 $\mu$M). The data from experiment 2 indicate that at 0 and 5 $\mu$M of synthetic genistein the number of nodules formed on plants at 17.5° C. RZT was higher than for plants at 15° C. RZT. However, between 10 and 40 $\mu$M, there was no difference in nodule number for plants at 17.5 and 15° C. RZT. At 20 $\mu$M the number of nodules formed at 17.5 and 15° C. was not different from the number formed at 25° C. A similar pattern of diminishing nodule number differences between 17.5 and 15° C. at higher synthetic genistein concentrations was also apparent in the data from experiment 1.

Genistein application also increased the total nodule mass of soybean plants at suboptimal RZT. In experiment 2, at 0 $\mu$M synthetic genistein, the plant nodule weights at 17.5 and 15° C. RZT were only 51.4 and 19.7%, respectively, of those of plants grown at 25° C. RZT. When the synthetic genistein concentration was 20 $\mu$M, the nodule weights of plants at 17.5° C. were not different from those of plants at 25° C. RZT, whereas nodule weights of plants at 15° C. RZT increased to 40.4% from 19.7% of that of plants grown at 25° C. RZT. The nodule mass data from plants with isolated genistein application from experiment 1 followed the same pattern. At 0 $\mu$M isolated genistein, the plant nodule weights at 17.5 and 15° C. RZT were 46.3 and 23.1%, respectively, of plants at 25° C. RZT, whereas at 20 $\mu$M isolated genistein these increased to 74.7 and 36.5%, respectively, of plants at 25° C. RZT.

Genistein Effects on $N_2$ Fixation

As indicated by the change in photosynthetic rate of uppermost fully expanded leaves, the onset of $N_2$ fixation by plants grown at 25, 17.5, and 15° C. RZT started at 19 to 21, 29 to 33, and 39 to 45 DAI, respectively. For plants grown at 17.5° C. RZT, the photosynthetic rate decreased with time prior to the onset of $N_2$ fixation, regardless of genestein treatment. However, when the photosynthetic rates recovered because of commencement of $N_2$ fixation, the photosynthetic recovery of plants inoculated with B. japonicum treated with 20 $\mu$M genistein occurred sooner than that of other treatments. At 31 DAI, the photosynthetic rate at 20 $\mu$M was higher than that of other genistein applications. Once all six treatments started fixing nitrogen and the photosynthetic rates had increased sharply, the photosynthetic rate assumed a pattern of gradual decline that was not different among treatments.

For plants at 15° C. RZT changes in photosynthetic rates over time were qualitatively similar to those of plants grown at 17.5° C. RZT, but the recovery of photosynthetic rates occurred later, between 39 and 45 DAI. Since plants that had received the 20 $\mu$M synthetic genistein treatment started fixing nitrogen earlier, the photosynthetic rate of these plants reached its peak value earlier. Also, because genistein application increased nodule number and hastened the onset of $N_2$ fixation, the total fixed nitrogen was higher in plants receiving 10 to 20 $\mu$M genistein at 17.5° C. RZT. At the lowest RZT (15° C.), genistein application increased the number of nodules, but measured total fixed $N_2$ did not appear to increase in either experiment. At 25° C. RZT the onset of $N_2$ fixation was not accelerated by genistein application.

Genistein application also led to an increased plant total dry weight at both 17.5 and 15° C. RZT. However, for other growth variables, such as leaf number and leaf area, no differences were found due to genistein treatments.

Microscopic Observations of Genistein Effects on Root Hair Curling and Infection The durations of the various morphological changes during the early nodule infection stages of soybean under optimal and suboptimal RZT conditions were reported by Zhang and Smith (1994). For the control plants (0 $\mu$M synthetic genistein) of this experiment maintained at 25° C. RZT, curled root hairs were observed 0.5 DAI and the initiation of infection threads occurred 1 DAI. For the plants grown at suboptimal RZTs, all infection steps were delayed. Root hair curling commenced within 1 day for plants at 17.5 or 15° C. RZT; however, this stage ended 1 DAI for the plants grown at 17.5° C. RZT and 2 DAI for the plants at 15° C. RZT. Root hair curling for plants that received synthetic genistein-treated bradyrhizobia was already complete by the time of the first observation (0.5 DAI) at all three RZTs. Infection thread initiation had commenced by 0.5 DAI for the plants grown under optimal RZT (25° C.) and within 1 DAI for control plants at the sub-optimal RZTs (17.5 and 15° C.). The times between Inoculation and the curling of the root hairs for control plants grown at 17.5 and 15° C. RZT were 0.5 and 1.5 days longer, respectively, than those of plants at 25° C. Application of 20 $\mu$M synthetic genistein shortened this stage, such that it was already complete by 1 DAI for all three RZTs. The frequency of curled root hairs for plants that had received *B. japonicum* preincubated with genistein was much higher than for plants that had received untreated bacterial cells (about 40 and 30% higher, respectively, for plants at 15 and 17.5° C. RZT).

Elongation of infection threads was not affected by genistein application. Infection threads of plants at 25° C. RZT reached the base of root hairs 2.5 DAI, for an elapsed time of 2 days after infection thread initiation. Infection thread growth of plants at the sub-optimal 5 RZTs (17.5 and 15° C.) was slowed, with infection threads reaching the base of the plant root hairs 5 and 8 DAI, respectively. The application of genistein did not shorten the elapsed time from infection thread initiation until the infection threads reached the base of the root hairs.

Discussion

Genistein application increased the number of nodules at suboptimal RZTs (17.5 and 15° C.). This increase occurred over a range of genistein concentrations at both 15 and 17.5° C. RZT. Genistein concentrations of 15 to 20 $\mu$M had the greatest effect on stimulation of nodulation. At optimal (25° C.) RZT, 5 $\mu$M genistein caused a numerical, but not a statistical increase in nodule number. There are three possible explanations for the stimulative effect of genistein at suboptimal RZT: (a) soybean plants are less able to synthesize signal molecules (including genistein) at suboptimal RZT, (b) soybean plants are less able to excrete signal molecules at suboptimal RZT, (c) bradyrhizobia are less sensitive to plant signal molecules at suboptimal RZT.

Genistein application increased the number of soybean nodules formed at 17.5 and 15° C. RZT. This could be due to an increase either in the number of infections initiated (as observed microscopically) or in the proportion of infections leading to nodule formation. In our experiments, preincubation with genistein at 30° C. prior to soybean inoculation activated the bradyrhizobial nod genes. The expression of the bradyrhizobial nod genes has been shown to stimulate production of the bacterial nod factor. This nod factor has been identified as a lipo-oligosaccharide that is able to induce many of the early events in nodule development, including deformation and curling of plant root hairs, the initiation of cortical cell division, and induction of root nodule meristems. Nodulation events started earlier at both of the suboptimal RZTs tested, presumably because the added genistein stimulated the production of the lipo-oligosaccharide.

The effect of genistein concentration increased with decreasing RZT. At suboptimal RZT (17.5 and 15° C.) the most effective concentrations were in the 15 to 20 $\mu$M range, whereas at optimal (25° C.) RZT there was some indication that 5 $\mu$M may have been effective. The the activation of *B. japonicum* nodABC-lacZ fusions by daidzein and genistein has been tested. It was showed that 5 $\mu$M genistein is sufficient to maximally induce the nodulation genes and higher concentrations did not inhibit nodule gene induction. Our results at 25° C. RZT confirmed the findings of Kosslak et al, (1987). However, the results at 17.5 and 15° C. RZT indicated that the rhizobial nod gene induction may be temperature dependent, at lower temperatures higher genistein concentrations were required to cause nodule number increases.

Although the number and size of nodules produced was increased by *B. japonicum* preincubated with genistein, nitrogen concentration of plants in experiment 1 and most shoot or root nitrogen concentrations in experiment 2 were not different, the exception being a genistein-produced increase in shoot nitrogen concentration of plants maintained at 17.5° C. RZT. This seems to indicate that the additional nodule mass formed by genistein stimulation at suboptimal RZT is inefficient. Other studies have also found that nodules formed at suboptimal RZT are less efficient. It was reported that the effect of low temperature on $N_2$ fixation and $N_3O$-nitrogen assimilation might be mediated via effects on photosynthesis or translocation, as has been demonstrated through photosynthetic limitation of nitrogenase activity. The effects of low temperature on the function of $N_2$ fixing nodules could also be due to changes in nodule $O_2$ permeability, although this remains to be investigated. Soybean plants export the nitrogen fixed in nodules mainly in the form of ureide, the solubility of which is low and decreases rapidly as temperature declines; suboptimal RZT may have limited the rate of export of fixed nitrogen from nodules, resulting in decreased nitrogenase activity. Decreased temperature has also been reported to result in progressively less bacteroid tissue inside nodules. The number and the mass of nodules for soybean plants maintained at 15° C. RZT were increased by genistein application, but the accumulation of nitrogen in the plants was not different among genistein treatments. However, for the plants inoculated by *B. japonicum* treated with genistein, the total nodule number increased and the onset of $N_2$ fixation was earlier; the total fixed nitrogen per plant increased because of increasing plant dry weight at 17.5° C. The lack of an effect at 15° C. RZT may be an artifact. These plants were harvested only one week after the onset of $N_2$ fixation, so that differences in the amounts of nitrogen fixed may not yet have been detectable.

Soybean is a subtropical legume that has been shown to have an optimal temperature range of 25 to 30° C. for nodulation. The time course of each nodulation stage under optimal RZT conditions has been well described. Bacterial attachment to root hairs occurs within minutes of inoculation and is followed, within 12 hours, by marked curling of short root hairs. Infection threads, first visible within 24 hours of inoculation, reach the base of the root hair by 48 hours after inoculation. However, Zhang and Smith (1994) found that at suboptimal RZT all of the infection steps were progressively delayed. For example, the period between inoculation and root hair curling was 1 and 2 days, respectively, for plants grown at 17.5 and 15° C. RZT compared to the 0.5 days for plants at 25° C. RZT. Application of 20 $\mu$M genistein shortened this stage, such that it was already complete by 1 DAI for all three treatment RZTs. Since genistein application accelerated nodulation at suboptimal temperatures, the onset of $N_2$ fixation by plants that received 20 $\mu$M genistein was 1 to 2 days earlier than by 0 $\mu$M control plants.

The two forms of genistein tested were not different with regard to effects on nodulation, $N_2$ fixation, and plant growth variables. Since the genistein types were prepared very differently but resulted in essentially the same effects on soybean nodulation and $N_2$ fixation, the effects observed in this study would appear to be attributable to genistein rather than to any contaminants in the genistein material used.

In summary, this is the first time an environmental variable, in this case suboptimal RZT, has been shown to adversely affect nodulation by a legume through disruption of interorganismal signal exchange. In this case, preincubation of *B. japonicum* with genistein reduced the time elapsed before the beginning of root hair curling at suboptimal RZT, shortened the time from inoculation to the onset of $N_2$ fixation, increased the number of nodules produced, increased the size of the nodules produced, increased the amount of nitrogen fixed and increased plant growth at suboptimal RZT but had little or no effect at optimal RZT. In this system the optimum signal (genistein) concentration was 15 to 20 μM. The genistein stimulation of nodulation was seen with genistein from two sources (extracted from soybean and chemically synthesized). Two separate experiments showed that genistein stimulation of nodulation occurred for many of the genistein concentrations (treatments) at both 17.5 and 15° C. RZT. The microscopic observations provided mechanistic data that support the macroscopic observations.

APPLICATION OF GENISTEIN TO INOCULA AND SOIL TO OVERCOME LOW SPRING SOIL TEMPERATURE INHIBITION OF SOYBEAN NODULATION AND NITROGEN FIXATION

Since genistein has been shown above as playing an important role as a signal molecule in the early stages of symbiosis establishment between soybean and *B. japonicum*, it was of interest to determine whether suboptimal RZTs disrupt inter-organismal signalling, and whether preincubation of *B. japonicum* with genistein could increase soybean nodulation and $N_2$ fixation under field conditions. Controlled environment investigations have demonstrated such an effect under sand-hydroponic conditions. As shown above, the preincubation of *B. japonicum* with genistein reduced the time elapsed before the beginning of root hair curling, shortened the time from inoculation to the onset of $N_2$ fixation, and increased the amount of total nitrogen fixed per plant at suboptimal RZTs (Zhang and Smith, 1895b Plant Phys. 108:961–968).

Site Preparation and Field Layout

Two experiments were included in this study, located at the Emile A. Lods Research Centre, McGill University, Macdonald Campus. Each of the experiments were carried out at two adjacent sites. At one site the soil was surface-sterilized by the application of methyl bromide (50 gm$^{-2}$) under a plastic canopy for 72 h (sterilized site). Three days elapsed between removal of the fumigation canopy and planting. At the other site the soil was unsterilized. The sterilized site was included to prevent possible competition from native *B. japonicum* or interference from other elements of the soil microflora that might obscure genistein preincubation effects. The first experiment included three factors: genistein application, *B. japonicum* strains and soybean cultivars. The experimental design was a 2×2×2 factorial organized in a randomized complete block split-plot with four replications. The main-plot units consisted of genistein application treatments, [0 and 20 μM (Zhang and Smith, 1995b)], while the combinations of two soybean cultivars, Maple Glen and AC Bravor, and two strains of *B. japonicum* [532C (Hume and Shelp. 1990) and USDA110] formed the sub-plotunits. Two factors were included in the second experiment, genistein application, and soybean cultivars. This experimental design was also arranged as a randomized complete block split-plot design with four replications. Two levels of genistein concentration, 0 and 20 μM, were arranged as main-plot units, and soybean cultivar, Maple Glen and AC Bravor, were the subplot units. For each replication of both experiments one plot of a non-nodulating Evans was included as control, for estimating plant seasonal nitrogen fixation. At the unsterilized site, each sub-plot (2×3 m) consisted of four rows of plants with 40 cm between rows. The space between plots was 80 cm and between replications 1 m. At the sterilized site, the size of each sub-plot was 1.6×2 m and consisted of three rows of plants, also with 40 cm between rows. The space between plots was also 80 cm and between replications, 2 m. The soil type was a Chicot light sandy loam. In the previous year, 1993, this experimental field had been planted with oat and barley, while in 1992 green manure alfalfa was produced in this area. The soil nitrogen available for soybean uptake was high and the average nitrogen accumulation in the non-fixing plants was 167 kg ha$^{-1}$. Potassium and phosphate were provided by the spring application of 340 kg ha$^{-1}$ of 5-20-20.

Inoculum Preparation

The inoculum was produced by culturing *B. japonicum* strains 532C and USDA110 in yeast extract mannitol broth in 2000 mL flasks shaken at 125 rpm at room temperature (23–25° C.). Strains 532C and USDA110 have been shown to perform reasonably well over a range of temperatures (Lynch and Smith, 1993a Physiol. Plant 88:212–202). For production of *B. japonicum* preincubated with genistein (4', 5, 7-Trihydroxyisoflavone, purity of 98%, Sigma. Mississauga, Ontario, Canada) 100 mL of a cell suspension from a three-day old (log phase 2×10$^9$ cells mL$^{-1}$) sub-culture were aseptically added to 500 mL of sterile genistein solution in a 2000 mL Erlenmeyer flask and incubated at 30° C. without shaking for 48 h (Halverson and Stacey. 1984). Following incubation, the cell suspensions were pelleted in sterile centrifuge tubes at 7000 g for 10 min, washed once with distilled water, and resuspended to an OD$_{620}$ of 0.08 (approximately 10$^8$ cells mL$^{-1}$).

Planting Methods

Seed of the soybean [*Glycine max* (L.) Merr.] cultivars 'Maple Glen' and 'AC Bravor' were surface-sterilized in sodium hypochlorite (2% solution containing 4 mL L$^{-1}$ Tween 20), then rinsed several times with distilled water. These cultivars were selected as they have been developed for production under the short season, cool conditions or eastern Canada and have performed well there. The seeds were hand-planted on May 11 and 18 at the unsterilized and sterilized sites, respectively. The delay in planting the sterilized site was due to the extra time required for the methyl bromide fumigation. Twenty mL of inoculum (for experiment 1), or 20 mL of either genistein solution or distilled water (for experiment 2) per one metre row were applied by syringe directly onto the seed in the furrow. The nsk of cross contamination was minimized throughout planting and all subsequent data collection procedures by alcohol sterilization of implements used. Following emergence, seedlings were thinned to achieve a stand of 500,000 plants ha$^{-1}$ (20 plants m$^{-1}$ of row).

$^{15}$N Application

To allow the measurement of seasonal $N_2$ fixation rates by the isotope dilution method, $^{15}$N was applied (1.2 kg ha$^{-1}$, 99% pure, Isotec Inc., Miamisburg, Ohio, USA) as double-labelled ammonium nitrate in solution, to a microplot of six plants (30×40 cm) within each subplot in the first three replications at both sites in both experiments. Each mioroplot was surrounded by plastic sheeting placed in the soil to a depth of 15 cm to prevent lateral soil losses of the labelled nitrogen. The labelled nitrogen was applied at growth stage V1 (the first unifoliate leaf).

Data Collection

Daily soil average temperatures at depths of 5 and 10 cm were recorded at the Macdonald Campus weather station, McGill University, Ste. Anne de Bellevue, Quebec, Canada, 500 m from the experimental field.

The onset of $N_2$ fixation was measured from one month after planting. Acetylene reduction activity assays were used as a +/− measure of nitrogenase activity. Four plants were randomly selected from each sub-plot. These plants were uprooted and detopped: the roots were exposed to 10% acetylene in a sealed one litre Mason jar for 10 minutes. A 0.5 mL gas aliquot was then extracted and analyzed by gas chromatography (Hardy et al., 1968). When acetylene reduction activity was detected in all the genistein application plots, the number, weight, and nitrogen concentration of nodules were measured.

The final nodulation data were taken from plants harvested on August 12. At this time the plants were at the R6 developmental stage. The plants to be harvested were uprooted, the roots were washed with distilled water and the nodules were removed, counted and weighed. Microplot materials were harvested by hand at harvest maturity, oven-dried at 70° C. for at least 48 h, and weighed. The seeds were threshed by hand and ground using a Moulinex coffee mill (Moulinex Appliances Inc., Virginia Beach, Va., USA). The above-ground plant tissue from each microplot was ground separately to pass a 1 mm screen of a Wiley mill (A. H. Thomas Co., Philadephia, Pa., USA). The nitrogen concentration of grain and other plant tissues was then determined by Kjeldahl analysis (Kjeltec system, Tecator A B, Hoganas, Sweden). Following Kjeldahl analysis, a sample of the distillate obtained from the microplot shoot and grain material was dried and the ammonium present converted to nitrogen gas by an adaptation of the Dumas method (Preston et al. 1981) before measuring the $^{15}N:^{14}N$ ratio of each sample by emission spectrometry (Jasco N-150 $^{15}N$ analyzer, Japan Spectroscopic Co., Tokoyo, Japan). The sensitivity of the spectrometer was generally in the range of ±0.005% and the correlation coefficient value on calibration curves with standards was always greater than 0.99. The proportion of the total plant nitrogen derived from $N_2$ fixation was then determined following the formula described in Lynch and Smith (1993b Plant Soll 157:288–303):

N% from fixation
=$\{1-[(^{15}N:^{14}N$ of fixing plant)/($^{15}N:^{14}N$ of control plant)]$\}\times 100$.

Statistical analysis

Results were analyzed statistically by analysis of variance using the Statistical Analysis System (SAS) computer package (SAS Institute Inc., 1988), except the onset of nitrogen fixation data (presented in Table 1). When analysis of variance showed significant treatment effects, the least significant difference (LSD) test was applied to make comparisons among the means at the 0.05 level of significance. The times of onset of $N_2$ fixation by soybean plants inoculated with *B. japonicum* preincubated either with or without genistein were compared by the McNemar test.

Results

Soil Temperature and Plant Development

The seasonal soil temperature data indicated that the average daily RZTs at depths of 5 to 10 cm were below 15° C. until early June, and remained well below 20° C. until mid July (FIG. 1). These conditions slowed the rate of seedling emergence and symbiotic establishment between soybean host plants and *B. japonicum*, particularly for the earlier-seeded plants of the unsterilized site. For the May 11 planting at the unsterilized site, seedlings emerged on May 25, 14 days after planting (DAP). The first trifoliate leaf occurred at 38 DAP, and flowering in mid-July. Plants seeded on May 18 at the sterilized site emerged at 9 DAP and the first trifoliate leaf occurred only 1 day later than plants in the unsterilized plots. Plants in the sterilized site flowered and reached physiological maturity (early September) at the same times as plants in the unsterilized site.

Native Soil *B. japonicum*

The plants at the unsterilized site in experiment 2 formed few nodules, and at physiological maturity there were less than three per plant, although the nodules were very large, having a per nodule weights that were almost 5 times larger than those on the plants of experiment 1. These result indicated that in the native soil population of *B. japonicum* at the unsterilized site was low. However, at the sterilized site, the fumigation with methyl bromide was not completely effective and the plants in experiment 2 formed reasonable nodule numbers. Because at least some contamination occurred at both sites, the non-nodulating plants were used as the reference for estimating seasonal $N_2$ fixation in both experiments. Because of the higher levels of contamination at the sterilized site, comparisons between *B. japonicum* strains could not be made with confidence. Results from the sterilized site, therefore, focus on the effect of genistein application, and the two way interaction between Genistein Application and Soybean Cultivars.

Genistein Effects on Nodulation and the Onset of Nitrogen Fixation

The acetylene reduction assay was used as a +/− indicator of the onset of nitrogen fixation in experiment 1 and showed that the genistein-pretreated *B. japonicum* resulted in a two to four days earlier onset of $N_2$ fixation on both the sterilized and unsterilized sites (Table 1).

TABLE 1

The time of onset of nitrogen fixation by soybean plants inoculated with *Bradyrhizobium japonicum* preincubated either with genistein at 20 μM or 0 μM at both the unsterilized and sterilized sites. The onset of nitrogen fixation was indicated by detection of acetylene reduction activity.
(data from experiment 1)

| site | genistein | Jun. 13 | Jun. 15 | Jun. 17 | Jun. 21 | Jun. 23 | Jun. 28 | Jun. 30 |
|---|---|---|---|---|---|---|---|---|
| unsterilized | 20 μM | 0/16 | 9/16 | 16/16 | — | — | — | — |
|  | 0 μM | 0/16 | 6/16 | 11/16 | — | — | — | — |
|  | probability | NS | 0.10 | 0.05 |  |  |  |  |
| sterilized | 20 μM | — | — | — | 0/12 | 4/12 | 12/12 | 12/12 |
|  | 0 μM | — | — | — | 0/12 | 1/12 | 10/12 | 11/12 |
|  | probability |  |  |  | NS | 0.10 | NS | NS |

Values in the table indicate the number of plots in which nitrogen fixation was detected over the total number of plots. Within each site, the data were compared by the McNemar test.

When acetylene reduction activity was detected in all genistein-treated plots (June 17) at both the unsterilized and sterilized sites, genistein preincubated both *B. japonicum* strains USDA110 and 532C increased nodule numbers for both cultivars of AC Bravor and Maple Glen. At the unsterilized site AC Bravor plants receiving genistein-preincubated *B. japonicum* contained 127% more nitrogen in their nodules than those receiving untreated *B. japonicum* (Table 2). The genistein treatment also increased AC Bravor nodule mass, both plant nodule weight and individual nodule weight, at early soybean growth stages (Table 2).

At crop physiological maturity, the combination of AC Bravor and application of *B. japonicum* preincubated with 20 $\mu$M genistein at the unsterilized site resulted in an increase in nodule number and nodule weight per plant

TABLE 2

Evaluation of main effect, two way interactions between genistein treatment and *Bradyrhizobium japonicum* strains, or genistein treatment and soybean cultivar, and three way interaction among those three factors for nodule number, nodule weight, and nodule nitrogen content at two harvest stages at the unsterilized site. (data from experiment 1)

| | | | | sampling on June 17 | | | | sampling on August 12 | | |
|---|---|---|---|---|---|---|---|---|---|---|
| | | | | | nodule weight (mg) | | nodule nitrogen | | | nodule weight (mg) |
| genistein | *B. japonicum* | cultivar | nodule no. plant$^{-1}$ | plant$^{-1}$ | nodule$^{-1}$ | (mg g$^{-1}$) | (mg plant$^{-1}$) | nodule no. | plant$^{-1}$ | nodule$^{-1}$ |
| 20 $\mu$M | USDA110 | AC Bravor | 23.77 | 26.20 | 1.09 | 25.84 | 0.69 | 55.85 | 512.13 | 9.17 |
| | | Maple Glen | 22.25 | 17.40 | 0.78 | 25.95 | 0.47 | 61.73 | 561.47 | 9.09 |
| | 532C | AC Bravor | 24.37 | 18.43 | 0.76 | 31.38 | 0.58 | 48.35 | 505.75 | 10.46 |
| | | Maple Glen | 23.60 | 21.63 | 0.91 | 30.77 | 0.64 | 56.03 | 415.21 | 7.41 |
| 0 $\mu$M | USDA110 | AC Bravor | 18.10 | 11.57 | 0.63 | 32.49 | 0.38 | 38.03 | 318.35 | 8.37 |
| | | Maple Glen | 19.30 | 15.77 | 0.82 | 33.09 | 0.56 | 72.28 | 608.50 | 8.41 |

| | | | | sampling on June 17 | | | | sampling on August 12 | | |
|---|---|---|---|---|---|---|---|---|---|---|
| | | cultivar | nodule no. | nodule weight (mg) | | nodule nitrogen | | nodule no. | nodule weight (mg) | |
| genistein | *B. japonicum* | nt$^{-1}$ | nodule$^{-1}$ | (mg g$^{-1}$) | | (mg plant$^{-1}$) | | plant$^{-1}$ | nodule$^{-1}$ | |
| | 532C | AC Bravor | 14.30 | 6.60 | 0.46 | 25.49 | 0.18 | 41.08 | 425.04 | 10.33 |
| | | Maple Glen | 19.00 | 18.56 | 0.98 | 28.00 | 0.50 | 75.35 | 669.95 | 8.89 |
| LSD$_{0.05a}$ | | | 4.84 | 4.99 | 0.46 | 5.97 | 0.14 | 17.52 | 21.79 | 4.21 |
| LSD$_{0.05b}$ | | | 4.69 | 4.83 | 0.98 | 6.77 | 0.15 | 18.69 | 22.57 | 4.50 |
| genistein | | | ** | ** | NS | NS | ** | NS | NS | NS |
| *B. japonicum* | | | NS | NS | NS | NS | NS | *** | NS | NS |
| cultivar | | | NS | NS | * | NS. | NS | *** | *** | *** |
| genistein**B. japonicum* | | | NS | NS | NS | ** | NS | NS | NS | NS |
| genistein*cultivar | | | NS | *** | *** | NS | *** | ** | ** | NS |
| genisteinB. japonicumcultivar | | | NS | NS | NS | NS | ** | * | NS | NS |

Values represent the five plants in the $^{15}$N microplot (area equal to 0.12 m$^2$) from each subplot unit. Means within the same column and *B. japonicum* strains or soybean cultivar were analyzed by an ANOVA protected LSD test. LSD$_{0.05a}$ is for comparison of means within the same main plot unit at 0.05 level and LSD$_{0.05b}$ is for comparison of means across levels of the main plot factor. *, , and * were signifcant differencew at 0.1, 0.05, and 0.01 levels, respectively.

Maple Glen, however, these variables were not increased by genistein application. At the sterilized site, the effects of genistein application showed the same general pattern for plant nodule weight as at the unsterilized site; however, the numerical differences were not statistically different (Table 3).

TABLE 3

Evaluation of main eftect and two way interactions between genistein treatment and soybean cultivar for nodule number, nodule weight, and nodule nitrogen content at two harvest stages at the sterilized site. (data from experiment 1)

| | | | sampling on June 17 | | | | sampling on August 12 | | |
|---|---|---|---|---|---|---|---|---|---|
| | | | | nodule weight (mg) | | nodule nitrogen | | | nodule weight (mg) |
| genistein | cultivar | nodule no. plant$^{-1}$ | plant$^{-1}$ | nodule$^{-1}$ | (mg g$^{-1}$) | (mg plant$^{-1}$) | nodule no. | plant$^{-1}$ | nodule$^{-1}$ |
| | AC Bravor | 37.67 | 14.56 | 0.38 | 59.00 | 0.86 | 80.31 | 255.13 | 3.18 |
| | Maple Glen | 32.00 | 15.85 | 0.50 | 73.67 | 1.17 | 60.44 | 238.00 | 3.93 |
| | AC Bravor | 36.00 | 13.43 | 0.35 | 59.13 | 0.79 | 82.31 | 208.15 | 2.52 |
| | Maple Glen | 37.75 | 14.47 | 0.39 | 73.50 | 1.06 | 61.50 | 243.13 | 3.95 |
| LSD$_{0.05a}$ | | 7.58 | 2.78 | 0.10 | 22.31 | 0.31 | 3.54 | 9.97 | 0.14 |
| LSD$_{0.05b}$ | | 10.14 | 9.29 | 0.17 | 30.09 | 0.20 | 3.23 | 9.27 | 0.07 |
| genistein | | NS | NS | NS | NS | NS | NS | NS | NS |
| cultivar | | NS | NS | ** | *** | *** | *** | NS | NS |
| genistein*cultivar | | NS | NS | NS | NS | NS | NS | * | * |

Values represent the five plants in the $^{15}$N microplot (area equal to 0.12 m$^2$) from each subplot unit. Means within the same column and *B. japonicum* strains or soybean culltivar were analyzed by an ANOVA protected LSD test. LSD$_{0.05a}$ is for comparison of means within the same main-plot unit at 0.05 level and LSD$_{0.05b}$ is for comparison of means across levels of the main plot factor. *, , and * were significant difference at 0.1, 0.05, and 0.01 levels, respectively.

(Table 2). At the sterilized site, genistein application did not cause any significant changes on nodule number and nodule mass.

Genistein and Seasonal $N_2$ Fixation

Seasonal $N_2$ fixation by AC Bravor plants treated with genistein increased by 65% by the N difference method and 63% by the $^{15}N$ dilution method at the unsterilized site (Table 4).

receiving preincubated-*B. japonicum* 532C was 47 and 9% higher than of those receiving *B. japonicum* 532C only, whereas both variables for Maple Glen plants receiving either preincubated-*B. japonicum* USDA110 or *B. japonicum* USDA110 only were not different at the unsterilized site (Table 4). At the sterilized site, however, *B. japonicum* strain, did not affect seasonal $N_2$ fixation for Maple Glen

TABLE 4

Evaluation of main effect, two way interactions between genistein application and *Bradyrhizobium japonicum* strain, or genistein application and soybean cultivar, and three way interactions among those three factors for fixed nitrogen, nitrogen concentration and yield at final harvest at the unsterilized site. (data from experiment 1)

|  |  |  | N-difference | | $^{15}N$ dilution | | | |
|---|---|---|---|---|---|---|---|---|
| Genistein | *B. japonicum* | cultivar | Total fixed N (kg ha$^{-1}$) | Fixed N as % of total plant N | Total fixed N (kg ha$^{-1}$) | Fixed N as % of total plant N | N concentration (mg g$^{-1}$) | N yield (kg ha$^{-1}$) |
| 20 µM | USDA110 | AC Bravor | 158.96 | 47.68 | 104.92 | 31.63 | 30.43 | 331.88 |
|  |  | Maple Glen | 106.69 | 41.22 | 73.26 | 27.96 | 32.94 | 258.70 |
|  | 532C | AC Bravor | 156.63 | 49.33 | 100.42 | 32.46 | 31.05 | 315.79 |
|  |  | Maple Glen | 166.53 | 50.20 | 130.99 | 39.74 | 32.41 | 331.23 |
| 0 µM | USDA110 | AC Bravor | 78.99 | 31.12 | 61.60 | 24.71 | 30.54 | 250.35 |
|  |  | Maple Glen | 113.73 | 40.75 | 77.55 | 27.63 | 29.26 | 278.42 |
|  | 532C | AC Bravor | 112.88 | 39.05 | 64.12 | 22.11 | 26.33 | 268.94 |
|  |  | Maple Glen | 139.05 | 45.59 | 88.68 | 29.17 | 29.91 | 303.75 |
| LSD$_{0.05a}$ |  |  | 29.56 | 5.16 | 18.86 | 5.64 | 2.86 | 20.58 |
| LSD$_{0.05b}$ |  |  | 30.21 | 3.63 | 25.34 | 7.31 | 3.14 | 22.08 |
| genistein |  |  | ** | *** | * | * | NS | * |
| *B. japonicum* |  |  | *** | *** | ** | NS | NS | ** |
| cultivar |  |  | NS | NS | NS | * | NS | NS |
| genistein**B. japonicum* |  |  | NS | NS | NS | * | NS | NS |
| genistein*cultivar |  |  | ** | *** | NS | NS | NS | * |
| genisteinB. japonicumcultivar |  |  | * | NS | ** | NS | NS | * |

Values represent the five plants in the $^{15}N$ microplot (area equal to 0.12 m$^2$) from each subplot unit. Means within the same column and *B. japonicum* strains or soybean cultivar were analyzed by an ANOVA protected LSD test. LSD$_{0.05a}$ is for comparison of means within the same main-plot unit at 0.05 level and LSD$_{0.05b}$ is for comparison of means across levels of the main plot factor. *, , and * were significant difference at 0.1, 0.05, and 0.01 levels, respectively. The increase was 23% and 43% at the sterilized site as measured by the N difference and $^{15}N$ dilution methods, respectively (Table 5).

TABLE 5

Evaluation of main effect, two way interactions between genistein application and soybean cuitivar for fixed nitrogen, nitrogen concentration and yield at final harvest at the sterilized site. (data from experiment 1)

|  |  | N-difference | | $^{15}N$ dilution | | | |
|---|---|---|---|---|---|---|---|
| Genistein | cultivar | Total fixed N (kg ha$^{-1}$) | Fixed N as % of total plant N | Total fixed N (kg ha$^{-1}$) | Fixed N as % of total plant N | N concentration (mg g$^{-1}$) | N yield (kg ha$^{-1}$) |
| 20 µM | AC Bravor | 164.34 | 52.40 | 91.77 | 29.52 | 28.90 | 331.15 |
|  | Maple Glen | 163.65 | 51.97 | 80.95 | 26.26 | 29.37 | 313.84 |
| 0 µM | AC Bravor | 133.82 | 42.27 | 64.40 | 20.63 | 27.98 | 283.80 |
|  | Maple Glen | 163.31 | 52.18 | 54.56 | 19.28 | 27.95 | 312.80 |
| LSD$_{0.05a}$ |  | 15.76 | 4.85 | 7.25 | 3.24 | 1.11 | 21.61 |
| LD$_{0.05b}$ |  | 14.68 | 5.84 | 9.54 | 5.76 | 1.27 | 23.30 |
| genistein |  | ** | * | *** | * | * | * |
| cultivar |  | * | NS | *** | ** | ** | NS |
| genistein*cultivar |  | ** | NS | ** | ** | ** | ** |

Values represent the five plants in the $^{15}N$ microplot (area equal to 0.12 m$^2$) from each subplot unit. Means within the same column and *B. japonicum* strains or soybean cultivar were analyzed by an ANOVA protected LSD test. LSD$_{0.05a}$ is for comparison of means within the same main-plot unit at 0.05 level and LSD$_{0.05b}$ is for comparison of means across levels of the main plot factor. *, , and * were significant difference at 0.1, 0.05, and 0.01 levels, respectively.

Genistein-preincubated *B. japonicum* increased total plant nitrogen yield of AC Bravor by 20% at the unsterilized site and by 17% at the sterilized site (Tables 4 and 5). As plant protein yield is generally calculated by simply multiplying N content by 6.25 the same increases apply to seed protein yield. Total plant seasonal $N_2$ fixation (by the $^{16}N$ dilution method) and total nitrogen yield of Maple Glen plants receiving either genistein treated inoculum or inoculum only (Table 5).

EXPERIMENT 2

In experiment 2, application of genistein onto seeds in the furrow increased the number of nodules at both the unsterilized and sterilized sites at the first sampling date (Table 6).

TABLE 6

Effects of genistein applied directly onto seed in furrow at the time of planting on plant nodule number and nodule weight at both the unsterilized and sterilized sites. (data from experiment 2)

| | | first sampling* | | | sampling on August 12 | | |
|---|---|---|---|---|---|---|---|
| | | | nodule weight (mg) | | | nodule weight (mg) | |
| site | genistein | nodule no. | plant$^{-1}$ | nodule$^{-1}$ | nodule no. | plant$^{-1}$ | nodule$^{-1}$ |
| unsterilized | 20 μM | 0.08 | — | — | 3.78 | 116.21 | 36.33 |
| | 0 μM | 0.05 | — | — | 1.76 | 78.49 | 44.60 |
| | probability | NS | — | — | NS | 0.05 | NS |
| sterilized | 20 μM | 35.50 | 11.65 | 0.32 | 58.25 | 263.22 | 4.58 |
| | 0 μM | 27.92 | 11.02 | 0.40 | 52.50 | 229.50 | 4.37 |
| | probability | 0.05 | NS | NS | NS | NS | NS |

*the data of first sampling was the same as experiment 1, for the unsterilized -- June 17, for the sterilized site -- June 30. Means within the same colume and site were analyzed by an ANOVA protected t test.

At crop maturity, nodule weight per plant was increased by genistein at the unsterilized site. Genistein application, in the absence of deliberate *B. japonicum* inoculation, also increased seasonal $N_2$ fixation at both the unsterilized and sterilized sites (Table 7). The final total nitrogen yield of plants directly receiving 20 μM genistein increased 25 and 26% compared to those receiving only distilled water at the unsterilized and sterilized sites, respectively.

TABLE 7

Effects of genistein directly applied onto soybean seed in the furrow at planting, on fixed nitrogen, nitrogen concentration and yield at both the unsterilized and sterilized sites. (data from experiment 2)

| | N-difference | | $^{15}$N dilution | | | |
|---|---|---|---|---|---|---|
| Treatment | Total fixed N (kg ha$^{-1}$) | Fixed N as % of total plant N | Total fixed N (kg ha$^{-1}$) | Fixed N as % of total plant N | N concentration (mg g$^{-1}$) | N yield (kg ha$^{-1}$) |
| | | | unsterilized site | | | |
| 20 μM genistein | 36.88 | 19.42 | 31.12 | 21.53 | 23.54 | 181.88 |
| 0 μM genistein | 4.66 | 2.07 | 28.93 | 13.07 | 20.02 | 145.69 |
| probability | 0.05 | 0.05 | NS | 0.05 | 0.05 | 0.05 |
| | | | sterilized site | | | |
| 20 μM genistein | 198.78 | 56.83 | 95.37 | 27.64 | 29.20 | 348.28 |
| 0 μM genistein | 127.40 | 45.67 | 13.22 | 19.33 | 27.79 | 276.90 |
| probability | 0.05 | 0.05 | 0.05 | 0.05 | 0.05 | 0.05 |

Values represent the five plants in the $^{15}$N microplot (area equal to 0.12 m$^2$) from each subplot unit. Means within the same column and site were analyzed by an ANOVA protected t test.

TABLE 8

Effects of genistein application, *B. japonicum* strains, and soybean cultivars for soybean leaf number and area, grain yield components, and final protein and grain yield at the unsterilized site. (data from experiment 1)

| | | | leaf (plant$^{-1}$) | | number (plant$^{-1}$) | | 100 seeds | yield (t ha$^{-1}$) | | |
|---|---|---|---|---|---|---|---|---|---|---|
| Genistein | *B. japonicum* | cultivar | number | area (cm$^2$) | pod | seed | weight (g) | grain protein | total protein | grain |
| 20 μM | USDA110 | AC Bravor | 22.27 | 1021.20 | 24.70 | 61.28 | 18.67 | 1.70 | 2.07 | 4.33 |
| | | Maple Glen | 17.33 | 669.85 | 24.60 | 61.10 | 18.69 | 1.34 | 1.75 | 3.43 |
| | 532C | AC Bravor | 28.80 | 798.65 | 27.03 | 64.08 | 19.62 | 1.67 | 2.12 | 4.05 |
| | | Maple Glen | 19.03 | 715.23 | 20.53 | 50.40 | 18.74 | 1.59 | 2.07 | 3.91 |
| 0 μM | USDA110 | AC Bravor | 17.97 | 861.53 | 19.65 | 41.60 | 18.95 | 1.37 | 1.56 | 3.45 |
| | | Maple Glen | 19.38 | 730.33 | 25.65 | 59.60 | 19.11 | 1.37 | 1.74 | 3.69 |
| | 532C | AC Bravor | 21.60 | 715.93 | 23.15 | 51.20 | 19.34 | 1.48 | 1.81 | 3.90 |
| | | Maple Glen | 18.53 | 743.78 | 24.28 | 61.85 | 19.01 | 1.52 | 1.89 | 4.01 |
| LSD$_{0.05a}$ | | | 5.32 | 106.18 | 5.20 | 10.22 | 1.11 | 0.16 | 0.20 | 0.37 |
| LSD$_{0.05b}$ | | | 6.69 | 100.26 | 7.34 | 9.58 | 1.68 | 0.17 | 0.23 | 0.30 |
| genistein | | | NS | ** | NS | ** | NS | ** | ** | *** |
| *B. japonicum* | | | NS | ** | *** | *** | *** | ** | ** | *** |
| cultivar | | | ** | NS | NS | NS | NS | NS | NS | NS |

TABLE 8-continued

Effects of genistein application, B. japonicum strains, and soybean cultivars for soybean leaf number and area, grain yield components, and final protein and grain yield at the unsterilized site. (data from experiment 1)

| Genistein | B. japonicum cultivar | leaf (plant$^{-1}$) | | number (plant$^{-1}$) | | 100 seeds | yield (t ha$^{-1}$) | | |
|---|---|---|---|---|---|---|---|---|---|
| | | number | area (cm$^2$) | pod | seed | weight (g) | grain protein | total protein | grain |
| genistein*B. japonicum | | NS | NS | NS | NS | NS | ** | ** | ** |
| genistein*cultivar | | * | * | *** | *** | NS | ** | ** | ** |
| genistein*B. japonicum*cultivar | | NS | NS | NS | NS | NS | NS | NS | ** |

Means of leaf number and area, nodule number and weight, pod and seed number represent four plants from each subplot unit, at crop maturity. Means of 100 seed weight and grain dry matter yield calculated from the one meter row of each subplot unit at harvest maturity. LSD$_{0.05a}$ is for comparison of means within the same main-plot unit and LSD$_{0.05b}$ is for comparison of means across levels of the main plot factor. NS, *, , and * indicated no significant difference or significant differences at the 0.1, 0.05, and 0.01 levels, respectively.

TABLE 9

Effects of and genistein application and soybean cultivars on soybean leaf number and area, grain yield components, and final protein and grain yield at the sterilized site. (data from experiment 1)

| Genistein | ciltivar | leaf (plant$^{-1}$) | | number (plant$^{-1}$) | | 100 seeds | yield (t ha$^{-1}$) | | |
|---|---|---|---|---|---|---|---|---|---|
| | | number | area (cm$^2$) | pod | seed | weight (g) | grain protein | total protein | grain |
| 20 μM | Ac Bravor | 34.56 | 874.31 | 27.75 | 65.44 | 16.12 | 1.58 | 2.07 | 4.21 |
| | Maple Glen | 33.57 | 852.36 | 22.08 | 58.67 | 17.41 | 1.54 | 1.96 | 4.09 |
| 0 μM | AC Bravor | 27.87 | 676.12 | 22.50 | 54.14 | 15.69 | 1.39 | 1.77 | 3.64 |
| | Maple Glen | 37.94 | 848.06 | 26.25 | 60.19 | 16.51 | 1.49 | 1.96 | 3.88 |
| LSD$_{0.05a}$ | | 9.31 | 125.00 | 3.71 | 10.66 | 0.54 | 0.17 | 0.19 | 0.45 |
| LSD$_{0.05b}$ | | 10.04 | 131.41 | 4.95 | 10.83 | 1.05 | 0.17 | 0.20 | 0.43 |
| genistein | | NS | NS | NS | * | NS | * | * | ** |
| cultivar | | NS | NS | NS | * | *** | NS | NS | NS |
| genistein*cultivar | | NS | ** | *** | * | NS | ** | ** | ** |

Means of leaf number and area, nodule number and weight, pod and seed number represeent four plants from each subplot unit, at crop maturity. Means of 100 seed weight and grain dry matter yield calculated from the one meter row of each subplot unit at harvest maturity. LSD$_{0.05a}$ is for comparison of means within the same main-plot unit and LSD$_{0.05b}$ is for comparison of means across levels of the main plot factor. NS, *, , and * indicated no significant difference or significant differences at the 0.1, 0.05, and 0.01 levels, respectively.

TABLE 10

Effects of genistein applied directly onto seed in furrow at the time of planting, and soybean cultivar on soybean leaf number and area, grain yield components, and final protein and grain yield at the unsterilized site. (data from experiment 2)

| Genistein | cultivar | leaf (plant$^{-1}$) | | number (plant$^{-1}$) | | 100 seeds | yield (t ha$^{-1}$) | | |
|---|---|---|---|---|---|---|---|---|---|
| | | number | area (cm$^2$) | pod | seed | weight (g) | grain protein | total protein | grain |
| 20 μM | AC Bravor | 27.48 | 881.60 | 21.53 | 47.15 | 15.74 | 0.83 | 1.16 | 2.76 |
| | Maple Glen | 19.28 | 606.50 | 16.35 | 37.73 | 16.00 | 0.86 | 1.12 | 2.72 |
| 0 μM | AC Bravor | 22.03 | 722.98 | 15.73 | 28.53 | 15.33 | 0.78 | 0.92 | 2.24 |
| | Maple Gien | 16.65 | 500.58 | 15.45 | 35.05 | 16.18 | 0.73 | 0.94 | 2.41 |
| LSD$_{0.05a}$ | | 3.67 | 149.91 | 2.75 | 8.37 | 7.64 | 0.15 | 0.18 | 0.31 |
| LSD$_{0.05b}$ | | 5.72 | 157.61 | 2.72 | 10.05 | 7.36 | 0.17 | 0.19 | 0.34 |
| genistein | | NS | * | ** | * | NS | NS | ** | ** |
| cuitivar | | *** | ** | NS | * | NS | NS | NS | NS |
| genistein*cultivar | | NS | NS | ** | ** | NS | NS | NS | ** |

Means of leaf number and area, nodule number and weight, pod and seed number represent four plants from each subplot unit, at crop maturity. Means of 100 seed weight and grain dry matter yield calculated from the one meter row of each subplot unit at harvest maturity. LSD$_{0.05a}$ is for comparison of means within the same main-plot unit and LSD$_{0.05b}$ is for comparison of means across levels of the main plot factor. NS, *, , and * indicated no significant difference or significant differences at 0.1, 0.05, and 0.01 levels respeetively.

TABLE 11

Effects of genistein applied directly onto seed in furrow at the time of planting, and soybean cultivars on soybean leaf number and area, grain yield components, and final protein and grain yield at the sterilized site.
(data from experiment 2)

| | | leaf (plant$^{-1}$) | | number (plant$^{-1}$) | | 100 seeds | yield (t ha$^{-1}$) | | |
|---|---|---|---|---|---|---|---|---|---|
| Genistein | cultivar | number | area (cm$^2$) | pod | seed | weight (g) | grain protein | total protein | grain |
| 20 µM | AC Bravor | 34.13 | 971.75 | 26.13 | 62.00 | 16.58 | 1.77 | 2.13 | 4.53 |
|  | Maple Glen | 39.38 | 978.63 | 29.00 | 74.00 | 17.31 | 1.77 | 2.23 | 4.68 |
| 0 µM | AC Bravor | 38.63 | 679.67 | 20.17 | 48.00 | 15.30 | 1.43 | 1.80 | 3.94 |
|  | Maple Glen | 39.50 | 849.50 | 24.88 | 59.25 | 16.15 | 1.32 | 1.66 | 3.55 |
| LSD$_{0.05a}$ | | 14.27 | 57.99 | 4.54 | 11.34 | 1.88 | 0.24 | 0.28 | 0.41 |
| LSD$_{0.05b}$ | | 15.20 | 58.29 | 5.60 | 13.43 | 3.42 | 0.25 | 0.31 | 0.58 |
| genistein | | NS | *** | NS | * | NS | ** | ** | ** |
| cultivar | | NS | *** | ** | ** | NS | NS | NS | NS |
| genistein*cultivar | | NS | *** | NS | NS | NS | NS | ** | ** |

Means of leaf number and area, nodule number and weight, pod and seed number represent four plants from each subplot unit, at crop maturity. Means of 100 seed weight and grain dry matter yield calculated from the one meter row of each subplot unit at harvest maturity. LSD$_{0.05a}$ is for comparison of means within the same main-plot unit and LSD$_{0.05b}$ is for comparison of means across levels of the main plot factor. NS, *, , and * indicate no significant difference or significant differences at the 0.1, 0.05, and 0.01 levels, respectively.

Discussion

Genistein application increased the nodule numbers of both AC Bravor and Maple Glen plants at the first sampling date, and AC Bravor plants at the second sampling date at the unsterilized site (Table 2). At this site plants were sown on May 11, ten days before the normal planting date for soybean in this region. A similar increase in nodule number was not found at the sterilized site. The difference between the two sites may have been due to the different planting dates. At the unsterilized site the soil temperature at a depth of 5–10 cm was below 17° C. throughout the period between seeding and the time when the colour of the nodule centre changed from white to pink (two to three days before nitrogenase activity was detected, June 12). However, at the sterilized site, the 5–10 cm soil temperature was above 18° C. for almost two thirds of the time between germination and the onset of nitrogen fixation and above 20° C. for half this time. The preincubation of Bradyrhizobium with genistein has been shown to increase nodule numbers at lower RZT, and the effect of genistein application on nodule number and nitrogen fixation decreased with increasing RZT (Zhang and Smith, 1995b). Genistein application increased the number of nodules per plant at the unsterilized site. This could be due to an increase either in the number of infections initiated or in the proportion of infections leading to nodule formation, (Zhang and Smith, 1995b). At the final harvest, although nodule numbers were still numerically higher for the genistein treatments than the controls at the unsterilized site, they were not statistically different (Table 2).

At both the unsterilized and sterilized sites, the onset of nitrogen fixation by plants receiving bradyrhizobia preincubated with genistein was two to three days earlier than those receiving regular inoculum (Table 1). Soybean is a subtropical legume crop which has been shown to have an optimal temperature range of 25 to 30° C. for nodulation. The time-course of each nodulation stage under optimal RZT conditions has been well described. Bacterial attachment to root hairs occurred within minutes of inoculation and was followed, within 12 h, by marked curling of short root hairs. Infection threads, first visible within 24 h of inoculation, reached the base of the root hair by 48 h after inoculation. However, at suboptimal RZT all of the infection steps were progressively delayed (Zhang and Smith, 1994 J. Exp. Med. 279:1467–1473). For example, the period between inoculation and root hair curling was one and two days longer, respectively, for plants grown at 17.5 and 15° C. RZT than for plants at 25° C. RZT. It seems likely that preincubation of B. japonicum with genistein at 30° C. prior to soybean inoculation activated the bradyrhizobial nod genes. The expression of the bradyrhizobial nod genes should have stimulated production of the bacterial nod factor. This nod factor has been identified as a lipo-oligosaccharide, to induce many of the early events in nodule development, including deformation and curling of plant root hairs, the initiation of cortical cell division, and induction of root nodule meristems. Because the added genistein stimulated the production of the lipo-oligosaccharide, the period between inoculation and root hair curling was one to two days shorter (Zhang and Smith, 1995b). It seems very probable that preincubation of B. japonicum with genistein had the same effects in the field as in the controlled environment work, leading to accelerated nodulation and the onset of nitrogen fixation in cool spring soybean production areas.

Since the number and dry matter of nodules per plant were increased and the onset of nitrogen fixation was hastened by B. japonicum prelncubated with genistein, total fixed nitrogen and nitrogen yield per plant were increased (Tables 4 and 5). This agreed generally with our previous finding that genistein application increased total fixed nitrogen at 17.5° C. RZT, but not at 25° C. RZT, under controlled environmental conditions (Zhang and Smith, 1995b). It has been reported that the effect of low temperature on $N_2$ fixation and $NO_3$-nitrogen assimilation might be mediated via effects on photosynthesis or translocation. This has been demonstrated through photosynthetic limitation of nitrogenase activity. Soybean plants export the nitrogen fixed in nodules mainly in the form of ureide, the solubility of which is low and decreases rapidly as temperature declines; suboptimal RZTs may have limited the rate of export of fixed nitrogen from nodules, resulting in decreased nitrogenase activity. These studies indicate that nodules are less efficient at suboptimal RZT, especially when RZT is below 170° C. In contrast to our previous controlled environment study, in which RZTs were constantly maintained at 17.5 or 150° C. (Zhang and Smith, 1995), soil temperature generally increased throughout the first half at the soybean growing season under field conditions (FIG. 1). Therefore, the efficiency of the higher nodule numbers resulting from genistein application was not limited by soil temperature, and total fixed nitrogen and nitrogen yield of plants receiving preincubated *B. japonicum* with genistein were higher than those of plants receiving regular inoculum. Sprent (1979), speculated reported that an increase of ten percent in the period of nodule activity of a grain legume, particularly between the onset of $N_2$ fixation and the attainment of maximum fixation, could double the seasonal level of nitrogen fixed. In our experiment, the time of nodule function was about 70 days (late-June to early-September). Genistein application resulted in a two to four days increase in the duration of $N_2$ fixation (Table 1). Over the whole study, the total amount of nitrogen fixed was increased by approximately 40%. It seems likely that some of this increase in total fixed nitrogen was due to earlier nitrogen fixation hastened by genistein application under short season conditions, with the remainder due to the increased plant nodule numbers in the early vegetative growth stages.

The cultivar AC Bravor tended to be more responsive to inoculation with genistein-treated *B. japonicum* than Maple Glen at both the unsterilized and sterilized sites (Tables 4 and 5). AC Bravor is a later-maturing cultivar and has a higher potential yield than Maple Glen (Conseil Des Productions Végétales du Québec recommendations); however, at crop physiological maturity it had lower nodule numbers, nodule weight per plant and tissue nitrogen concentration than Maple Glen at the unsterilized site (Tables 2 and 4). Therefore, nitrogen limitation was more probable for AC Bravor growth and development. Increased nodule number and dry matter per plant of AC Bravor due to genistein application would have reduced nitrogen limitation; therefore, the total fixed nitrogen and nitrogen yield were greater than those of Maple Glen. At the sterilized site, the same pattern was found for nodule number (Tables 3 and 5). This showed that the effect of preincubation of *B. japonicum* with genistein on soybean nodulation and nitrogen fixation was more pronounced under plant nitrogen stress conditions. An interaction also existed with *B. japonicum* strain (Table 4). The combination of USDA110 with genistein resulted in greater increases in total fixed nitrogen, fixed nitrogen as a percentage of total plant nitrogen, and nitrogen yield than was the case for strain 532C.

One very interesting finding from the second experiment, those not deliberately inoculated with *B. japonicum*, was that the tissue nitrogen concentration and yield of plants inoculated with the genistein control solution were higher than those of plants which received neither *B. japonicum* nor genistein (Tables 6 and 7). It would seem that there are three possible explanations for the stimulative effect of genistein applied directly onto the soil. First, since genistein has been isolated and identified as a major inducer of nod genes in *B. japonicum*), genistein could have increased the infection rate by endogenous *B. japonicum*, resulting in increased soybean nodulation and $N_2$ fixation (Tables 6 and 7). In support of this possibility directly applied genistein onto the seed furrow at the planting time increased nodule numbers (Table 6). Second, increased total fixed nitrogen and nitrogen yield could be partially due to other functions of genistein. It has been reported that this isoflavone and its derivatives appear to be involved In resistance to both insects and fungi. Flavonoids can also function as modulators of polar auxin transport. Third, genistein could have stimulated other beneficial soil microorganism, such as mycorrhizal fungi, leading to a stimulation overall growth which would have resulted in greater nodulation and nitrogen fixation.

In summary, this is the first field research showing that preincubation of *B. japonicum* with genistein, or directly applied genistein into plant rhizosphere increased soybean nodulation and nitrogen fixation. Four separate experiments have all demonstrated the stimulative effects of genistein. Genistein application increased nodule number and nodule dry matter per plant and hastened the onset of nitrogen fixation, especially for early-planted soybean (unsterilized site). Total fixed nitrogen, fixed nitrogen as a percentage of total plant nitrogen, and total nitrogen yield all increased due to genistein application. Interactions existed between genistein application and soybean oultivars, and indicated that genistein applied to more nitrogen-stressed plants was more effective Wherever adequate *B. japonicum* soil populations existed it seems that *B. japonicum* nod genes could be stimulated by simple addition of genistein to the soil. Overall, from this study it is clear that preincubation of *B. japonicum* with genistein can increase soybean nodulation and nitrogen fixation.

INOCULATION OF SOYBEAN (*Glycine max.* (L.) Merr.) WITH GENISTEIN-PREINCUBATED *Bradyrhizobium japonicum* OR GENISTEIN DIRECTLY APPLIED INTO SOIL INCREASES SOYBEAN PROTEIN AND DRY MATTER YIELD UNDER SHORT SEASON CONDITIONS After having demonstrated that genistein-preincubated *B. Japonicum* or genestein applied directly to the rhizosphere can increase soybean nodulation and N fixation, field studies were performed to assess whether genistein could also increase soybean grain and protein yield.

Site Preparation and Field Layout

The two experiments included in this study were located at the Emile A. Lods Research Centre, McGill University, Macdonald Campus. The experiments were carried out on two adjacent sites, both on a Chicot light sandy loam soil. At one site, to prevent possible competition from native Bradyrhizobium or interference from other soil microflora that might obscure genistein preincubation effects, the soil was surface-sterilized by the application of methyl bromide (50 g m−2) under a plastic canopy for 72 h (sterilized site) Three days elapsed between removal of the fumigation canopy and planting (Lynch and Smith, 1993b). At the other site the soil was unsterilized. The first experiment included three factors, genistein application, *B. japonicum* strains, and soybean cultivars. The experimental design was a 2×2×2 factorial organized in a randomized complete block split-plot with four replications. The main-plot units consisted of genistein application treatments [0 and 20 mM, (Zhang and Smith, 1995)], while the combinations of two soybean cultivars, Maple Glen and AC Bravor, and inoculation treatments [two strains of *B. japonicum*, 532C (Hume and Shelp, 1990) and USDA110] formed the sub-plot units. Two factors were included in the second experiment, genistein application, and soybean cultivars. This experimental design was also arranged as a randomized complete block split-plot design with four replications. Two levels of genistein concentration, 20 and 0 mM, were arranged as mainplot units, and soybean cultivars, Maple Glen and AC Bravor, were the sub-plot units. At the unsterilized site, each sub-plot (2×3 m) consisted of four rows of plants with 40 cm between rows. The space between plots was 80 cm and between replications 1 m. At the sterilized site, the size of each sub-plot was 1.6×2 m and consisted of three rows of plants, also with 40 cm between rows. The space between plots was also 80 cm and between replications, 2 m. In the previous year, 1993, this experimental field had been planted with oat and barley, while in 1992 green manure alfalfa was grown in this experimental area. The available soil nitrogen, indicated by the average nitrogen accumulation in the non-fixing soybean plants, was 167 kg ha−1. Potassium and phosphate were provided by a spring application of 340 kg ha−1 of 5-20-20 (N, $P_2O_5$, $K_2O$). The 5 kg ha−1 of nitrogen were applied as "popup" nitrogen, conventionally applied in this area to help support plant growth before the onset of nitrogen fixation.

Inoculum Preparation

For the first experiment, the inoculum was produced by culturing, separately, B. japonicum strains 532C and USDA110 in yeast extract mannitol broth (Vincent, 1970) for 3 d in 2 L flasks shaken at 125° rpm at room temperature (20–23° C.). For production of B. japonicum preincubated with genistein (4', 5, 7-Trihydroxyisoflavone, purity of 98%, Sigma, Mississauga, Ontario, Canada), 100 mL of a cell suspension from a 3-day old (log phase, 2×109 cells mL-1) sub-culture were aseptically added to 500 ml of sterile genistein solution (24 μM, which made the final genistein concentration equal to 20 mM) in a 2 L Erlenmeyer flask and incubated at 30° C. without shaking for 48 h. Following incubation, the cell suspensions were pelleted by centrifugation at 7000 g for 10 min, washed once with distilled water, and resuspended in distilled water to an A620 of 0.08 (approximately 108 cells mL-1).

Planting Method

Seeds of the soybean cultivars 'Maple Glen' and 'AC Bravor' were surface-sterilized in sodium hypochlorite (2% solution containing 4 mL L-1 Tween 20), then rinsed several times with sterile distilled water. These cultivars were selected as they have been developed for production under the short season, cool conditions of eastern Canada and have performed well there. The seeds were planted by hand on May 11 (about one week before the normal planting date) and 18 (approximately the middle of the normal planting period) at the unsterilized and sterilized sites, respectively. The delay in planting at the sterilized site was due to the extra time required for the methyl bromide fumigation. Twenty mL of washed inoculum (for experiment 1), or 20 mL of either genistein solution (20 μM) or distilled water (for experiment 2) per one metre of row were applied evenly by syringe directly onto theseed along the furrow. Alcohol sterilization of the implements was used to prevent cross contamination throughout planting and all subsequent data collection procedures. Following emergence, seedlings were thinned to achieve a stand of 500,000 plants ha-1 (20 plants m-1 of row, with an average inter-plant distance of 5 cm within the row).

Data Collection

Daily average air temperature, average soil temperatures at a depth of 5 cm and precipitation were recorded at the Macdonald Campus weather station, McGill University, Ste. Anne de Bellevue, Quebec, Canada, only 500 m from the experimental field. Plant samples were taken on August 12, at which time plants were at the reproductive stage 6 (R6), for investigation of growth variables such as, leaf number, leaf area, pod number and seed number. Leaf number and area per plant were determined using a Delta-T area meter (Delta-T Devices Ltd., Cambridge, UK). Pod number and seed number per plant were counted by hand. End of season grain yield was determined from a one meter row of plants taken from the middle row of each plot. Plants were harvested by hand at harvest maturity, then shelled by a plot combine (wintersteiger, Salt Lake City, Utah), oven-dried at 70° C. for at least 48 h, and weighed. Grain dry matter yield was calculated based on a 0% moisture content. Six more plants, also from the middle row, were hand-harvested. and oven-dried at 70° C., after which the seeds were manually separated from shoots. Total shoot weight and harvest index were determined from these plants, which were enclosed within wire mesh following flowering to facilitate the collection of senescent leaves. The dried seeds from each plot were ground using a Moulinex coffee mill (Moulinex Appliances Inc., Virginia Beach, Va.). The nitrogen concentration of seeds was then determined by Kjeldahl analysis (Kjeltec system, Tecator AB, Hoganas, Sweden). The protein concentration was calculated by multiplying nitrogen concentration by 6.25.

Statistical Analysis

Results were analyzed statistically by analysis of variance using the Statistical Analysis System (SAS) computer package (SAS Institute Inc., 1988). When analysis of variance showed significant treatment effects, the least significant difference (LSD) test was applied to make comparisons among the means at the 005 level of significance.

Results

Air and soil temperature, precipitation and plant development Average daily temperatures for both air and soil (at a depth of 5 cm) were below 15° C. until early June, and remained well below 20° C. until mid-July, about two months after planting. Both low air and soil temperatures slowed the rate of seedling emergence, particularly for the earlier-seeded plants at the unsterilized site (Zhang and Smith, unpublished data), such that for the May 11 planting at the unsterilized site, seeds germinated on May 25, i.e. at 14 days after planting (DAP), while seeds planted on May 18 at the sterilized site germinated at 9 DAP. Plants in both the unsterilized and sterilized sites flowered in mid-July and reached physiological maturity in early September. Precipitation during the planting period was 47 mm, while the total precipitation during the soybean growing season (May to September) was 572 mm, which is sufficient for soybean production.

EXPERIMENT 1

The nodule number of uninoculated plants in experiment 2 indicated that the native soil population of B. japonicum in unsterilized soil was low, with uninoculated plants forming few nodules; at physiological maturity there were fewer than three nodules per plant, although the nodules were very large, on average almost 5 times larger than those on plants in experiment 1. However, at the sterilized site, fumigation with methyl bromide was not completely effective and the un-inoculated plants in experiment 2 formed nearly as many nodules as the inoculated plants in experiment 1. Therefore, main effects, two way interaction comparisons between either genistein application and B. japonicum strains, or genistein application and soybean cultivars and three way interaction comparisons for genistein application, B. japonicum strains, and cultivars were tested on the unsterilized site. At the sterilized site, only main effects and two way interactions between genistein application and soybean cultivars were tested. Most growth variables, such as plant height, nodule number per plant, time of crop maturity, harvest index, and seed moisture content at harvest maturity, were not affected by genistein application at both the unsterilized and sterilized sites (data not shown). The leaf area of AC Bravor receiving USDA110 was increased by 20 μM genistein addition at the unsterilized site (Table 8). At the sterilized site, the leaf area of AC Bravor was increased more by 20 μM genistein application than the leaf areaof Maple Glen (Table 9).

The number of seeds formed on AC Bravor plants receiving genistein-preincubated B. japonicum (Experiment 1) increased by 34.2 and 20.9% compared to those receiving B. japonicum only at the unsterilized and sterilized sites, respectively (Tables 8 and 9). This increase in seed number was due to the higher pod numbers of AC Bravor plants receiving genistein-preincubated *B. japonicum* than of those receiving *B. japonicum* only. Maple Glen plants receiving either genistein-preincubated *B. japonicum* or *B. japonicum* only had a similar seed number at both the unsterilized and sterilized sites (Tables 8 and 9). Since seed number of AC Bravor increased, the total grain yield was increased by genistein application at both the unsterilized and sterilized sites. At the unsterilized site, grain yield of AC Bravor plants receiving preincubated-*B. japonicum* USDA110 was 25.5% higher than by those receiving *B. japonicum* USDA110 only, whereas grain yield of AC Bravor plants receiving either preincubated-*B. japonicum* 532C or *B. japonicum* 532C only was not different between these treatments (Table 8). At the sterilized site, the final grain yield of AC Bravor treated with genistein increased due to the increase in seed number, and was 15.7% higher than that of plants without genistein treatment (Table 9). Grain protein yield and total plant protein yield of AC Bravor were increased by genistein application at both the unsterilized and sterilized sites (Tables 8 and 9). For the two *B. japonicum* strains, USDA110 and 532C, the grain protein yield of AC Bravor with genistein treatment was 21.6 and 13.7% higher than in plants without genistein treatment at both the unsterilized and sterilized sites, respectively. There was no difference in protein yield between Maple Glen receiving either preincubated-*B. japonicum* or normal *B. japonicum* at either the unsterilized or sterilized site. Two way interactions between genistein application and *B. japonicum* also existed at the unsterilized site: the grain protein yield of plants inoculated with genistein-preincubated *B. japonicum* USDA110 increased by 13.4% compared to *B. japonicum* USDA110 without genistein, whereas preincubation of *B. japonicum* 532C with genistein did not increase grain protein yield (Table 8). The effects of genistein application on total plant protein yield followed the same pattern as grain protein yield at both the unsterilized and sterilized sites (Tables 8 and 9); however, total plant protein yield of plants receiving genistein-preincubated *B. japonicum* 532C was 13.5% higher than that of plants receiving *B. japonicum* 532C without genistein at the unsterilized site (Table 8).

EXPERIMENT 2

Genistein, directly applied onto seeds in the furrow at the time of planting, increased soybean growth variables and yield compared to control plants at both the unsterilized and sterilized sites (Tables 10 and 11). Generally speaking, the effects of genistein application directly onto soil, without preincubated *B. japonicum*, on soybean growth variables, yield components, and final grain and protein yield in experiment 2 followed the same pattern as was observed in experiment 1.

Discussion

Genistein is one of the plant-to-bacteria signals important in establishment of the soybean-Bradyrhizobium symbiosis (Kosslak et al.,1987). Preincubation of *B. japonicum* inocula with genistein increased nodule number and hastened the onset of N2 fixation at suboptimal RZTs under controlled environment conditions (Zhang and Smith, 1995). These increases could lead to an increase in nitrogen fixation ability and a reduction in the nitrogen limitation of soybean growth in short season areas. Therefore, the genistein-pretreated *B. japonicum* increased the final grain yield at both the unsterilized and sterilized sites (Tables 8 and 9). For instance, at the unsterilized site the yield of AC Bravor receiving *B. japonicum* USDA110 was increased by 25.5% (Table 8).

Genistein application not only increased plant dry matter accumulation, but also increased total protein and grain protein yield for AC Bravor (Table 8). Zhang and Smith (1994) reported that low RZTs delay all of the steps in the infection of soybean roots by bradyrhizobla. For example, the period between inoculation and root hair curling was 1 and 2 clays longer, respectively, for plants grown at 17.5 and 15° C. RZT than at 25° C. RZT. Presumably, the preincubation of *B. japonicum* with genistein at 30° C. prior to soybean inoculation activated the bradyrhizobial nod genes. Since added genistein activated bradyrhizobial nod genes and soybean inoculation, nodulation events and nitrogen fixation started 2 to 5 days earlier at the suboptimal RZTs (Zhang and Smith, 1995). It was postulated that an increase of 10% in the period of nodule activity of a grain legume, particularly between the onset of nitrogen fixation and the attainment of maximum fixation, could double the seasonal level of nitrogen fixed. In a controlled environment experiment, the Total fixed nitrogen of plants receiving 20 mM genistein-pretreated *B. japonicum* increased by 49.5 and 43.7% compared to non-genistein pretreated *B. japonicum* at 17.5 and15° C., respectively (Zhang and Smith, 1995). Also, an increase of 40% in total fixed nitrogen was obtained from a field experiment under the short soybean growing season conditions typical in Canada. In the present application, the increased grain protein yield and total protein yield at both the unsterilized and sterilized sites agrees with the findings discussed above.

In experiment 2, genistein applied directly onto seeds in the furrow at the time of planting also increased yield components and final grain and protein yield for both cultivars, AC Bravor and Maple Glen, at the sterilized site, and for AC Bravor only at the unsterilized site (Tables 10 and 11). As the plants were not deliberately inoculated with *B. japonicum* in this experiment, the observed increases would seem to have two possible explanations. First since genistein has been isolated and identified as a major inducer of nod genes in *B. japonicum* (Kosslak et al., 1987), genistein could have induced nod gene expression in the native soil *B. japonicum*, resulting in increased soybean nodulation and nitrogen fixation. Second, increased protein yield and grain yield could be due to the growth regulator effects reported for similar compounds. Flavonoids have been reported to function as modulators of polar auxin transport. However, given the small amounts of genistein added and the previously measured effects on soybean nodulation, the former of these two possibilities seems most probable. Some additional mechanisms could also have effects, although they seem unlikely to be major in this case. A recent study indicated that low molecular weight phenolic compounds not only play important roles in the plant-(Brady)Rhizobium symbiosis, but also stimulate the early events of vesicular arbusoular mycorrhizal establishment. It was reported that an isoflavone and its derivatives appear to be involved in resistance to both insects and fungi.

The proportional increases in average values of plant growth variables, yield components and final grain and protein yield were generally larger in experiment 2 than in experiment 1. Two possible conditions could have led to this observation. First, native bradyrhizobia proliferated and developed under low soil temperature conditions (below 15° C.) until early June (when nodules were visible). At the time when nitrogen fixation was first detected genistein addition to the soil increased nodule number by 60 and 27% at the unsterilized (June 11) and sterilized (June 17) sites, respectively. At physiological maturity (August 11), soil applied genistein increased nodule number by 15 and 12%, respectively, at the sterilized and unsterilized sites. For plants inoculated with *B. japonicum*, the onset of nitrogen fixation started 3 d earlier and at this time nodule numbers were higher with genistein addition at the unsterilized site. Nodule numbers were not different between genistein levels at the times of either onset of nitrogen fixation at the sterilized site, or at physiological maturity at both sites. Second, soils were not inoculated with *B. japonicum* in experiment 2, and so would have had lower *B. japonicum* populations than the inoculated soils of experiment 1. This resulted in lower nodulation and rates of N2 fixation, therefore, plants in the uninoculated soils would have had a greater nitrogen deficiency stress. These plants would benefit more from a treatment that made the symbiosis more effective.

The cultivar AC Bravor tended to be more responsive to genistein application at both sites for experiment 1 and at the unsterilized site for experiment 2. At the sterilized site of experiment 2 the increases in growth variables, yield components, and final grain and protein yield of Maple Glen were similar to those measured for AC Bravor (Tables 8–11). AC Bravor is a relatively late-maturing cultivar in its production region and has a higher potential yield than Maple Glen, under optimal environmental conditions (Conseil Des Productions Végétales du Québec recommendations). Thus, nitrogen limitation was more for AC Bravor growth and development. Since the effect of preincubation of *B. japonicum* with genistein on soybean nodulation and nitrogen fixation was more pronounced under plant nitrogen stress conditions, the increase in grain yield and protein yield by AC Bravor due to genistein application should be greater than that of Maple Glen.

In summary, with the experiments described above, this is the first field experiment showing that genistein-preincubated *B. japonicum* increased soybean grain and protein yield. Interactions existed between genistein application and soybean cultivars, suggesting that genistein application to higher yield potential cultivars was more effective. Genistein directly applied into the rhizosphere also improved plant grain and protein yield, probably by stimulation of native soil *B. japonicum*. Overall, from this study it is clear that genistein-preincubated *B. japonicum*, or genistein directly applied onto seed in the furrow at the time of planting can increase soybean grain yield, grain protein yield, and total protein yield.

OTHER ENVIRONMENTAL FACTORS WHICH INHIBIT OR DELAY NODULATION OF SOYBEAN

Optimal temperatures for symbiotic nitrogen fixation by *B. japonioum* range from 25 to 35° C., and temperatures outside this range are inhibitory. As shown previously, suboptimal temperatures affect early stages of nodulation. As shown above, under low temperature conditions, incubation of *B. japonicum* with genistein prior to inoculation of soybean resulted in reduction of the time elapsed before both the beginning of root hair curling and the onset of nitrogen fixation, and increased the total amount of nitrogen fixed per plant. In order to investigate whether temperature conditions affected the sensitivity of *B. japonicum* to plant-to-bacterial signal molecules, the expression of the isoflavone-inducible nodY-ABC operon of *B. japonicum* was measured by assaying β-galactosidase activity from the nodY-lacZ transitional gene fusion in *B. japonicum* strain ZB977. This strain is *B. japonicum* strain USDA1110 harboring plasmid pZB32 which is a translational fusion between the *B. japonicum* nodY open reading frame and *E. coli* β-galactosidase. Hence, the level of β-galactosidase activity reflects expression of the flavonoid-inducible nod genes. Induction of nodY-lacZ expression by different concentrations of genistein was monitored for 24 hrs. This analysis indicated that different genistein concentrations are required for maximal nod gene induction at different temperatures. For example, 5 µM genistein, the lowest concentration tested, was the most effective concentration at 30 and 25° C. However, at 15 and 10° C., the most effective genistein concentrations were 15 and 20 µM, respectively. Significantly, the peak nodY-lacZ at 25° C. was over 5 fold greater than at 15° C., and was attained with a 4 fold lower genistein concentration.

In order to insure that the variations in response to genistein are not simply a reflection of temperature effects on general cell metabolism, optical density of the culture was monitored as a measurement of growth at the different temperatures. Although this experiment demonstrated that temperature has a dramatic effect on culture growth, with very little growth occurring at 10 to 15°, it was interesting to note that the rate of cell growth was greater at 30 than at 25° C. (data not shown). Strikingly, nodY-lacZ induction levels are greater at 25 than at 30°. It was also verified that the levels of nodY-lacZ expression did not simply reflect growth rate (data not shown).

FIG. 3 therefore corroborates the field studies described above by showing that at low temperatures, *B. japonicum* is less sensitive to plant-to-bacterial signals. Thus, suboptimal temperatures inhibit both the biosynthesis of genistein in soybean tissue and reduced the sensitivity of *B. japonicum* to flavonoid signals.

Strikingly, FIG. 3 also shows that at 30° C., at all the genistein concentrations tested, *B. japonicum* has a reduced sensitivity to genistein. This result therefore suggests that the present invention can find applicability for growth of legumes under supra-optimal conditions.

It has also been demonstrated that when the first cohorts of nodules start to fix nitrogen, the concentration of genistein in root tissues significantly decreases. Presumably, upon the initiation of nitrogen fixation, there is no immediate need for the production of new nodules and new symbiosis, and hence, the genistein concentration drops and nodulation slows down. In essence therefor, nitrogen fixation is itself a nodulation inhibiting environmental factor.

Strinkingly, it was found that watering of plants with a solution comprising genistein, at the point when nitrogen fixation starts and genistein concentration decreases, permits nodulation to persist (data not shown). This should enable an increase in protein and grain yield of the soybean. Since high nitrogen concentration in the soil can be considered another environmental factor that inhibits nodulation, the present invention provides a means to overcome this nodulation inhibition.

Although the present invention has been described hereinabove by way of preferred embodiments thereof, it can be modified, without departing from the spirit and nature of the subject invention as defined in the appended claims.

What is claimed is:

1. A method for enhancing grain yield of soybean grown in the field under low root zone temperatures, comprising a treatment in the vicinity of one of a seed and root of said soybean with a composition comprising an agriculturally effective amount of a nodulation gene-inducing compound in admixture with an agriculturally suitable carrier medium, wherein said effective amount enhances grain yield of said soybean grown in the field under said low root zone temperatures in comparison to an untreated soybean grown under the same conditions, and wherein said low root zone temperatures are below about 25° C.

2. The method of claim 1, wherein said composition comprises a flavonoid compound.

3. The method of claim 2, wherein said flavonoid compound is selected from the group consisting of genistein and daidzein.

4. The method of claim 3, wherein a rhizobial strain which nodulates said soybean is exposed to a concentration of genistein ranging from about 5 µM to about 40 µM.

5. The method of claim 4, wherein said genistein concentration ranges from about 15 µM to about 20 µM.

6. The method of claim 4, wherein said low root zone temperatures are below about 25° C. to about 17° C.

7. The method of claim 4, wherein said low root zone temperatures are from about 17° C. to about 10° C.

8. The method of claim 1, wherein said low root zone temperatures are from about 17° C. to about 10° C.

9. A method for enhancing grain yield of soybean grown in the field under low root zone temperatures, comprising:
   a) incubating a rhizobial strain which nodulates said soybean with a composition comprising an agriculturally effective amount of a nodulation gene-inducing compound, in admixture with an agriculturally suitable carrier medium, wherein said effective amount enhances grain yield of said soybean grown in the field under said low root zone temperatures in comparison to an untreated soybean grown under the same conditions; and
   b) inoculating in the vicinity of one of a seed and root of said soybean said rhizobial strain of a), wherein said low root zone temperatures are below about 25° C.

10. The method of claim 9, wherein said composition comprises a flavonoid compound.

11. The method of claim 10, wherein said flavonoid compound is selected from the group consisting of genistein and daidzein.

12. The method of claim 11, wherein said rhizobial strains exposed to a concentration of genistein ranging from about 5 µM To about 40 µM.

13. The method of claim 12, wherein said genistein concentration ranges from about 15 µM to about 20 µM.

14. The method of claim 12, wherein said low root zone temperatures are below about 25° C. to about 17° C.

15. The method of claim 12, wherein said low root zone temperatures are from about 17° C. to about 10° C.

16. A method for enhancing nodulation of soybean grown in the field under low root zone temperatures, comprising a treatment in the vicinity of one of a seed and root of said soybean with a composition comprising an agriculturally effective amount of a nodulation gene-inducing compound in admixture with an agriculturally suitable carrier medium, wherein said effective amount enhances nodulation of said soybean grown in the field under said low root zone temperatures in comparison to an untreated soybean grown under the same field conditions and wherein said low root zone temperatures are below about 25° C.

17. The method of claim 16, wherein said composition comprises a flavonoid compound.

18. The method of claim 17, wherein said flavonoid compound is selected from the group consisting of genistein and daidzein.

19. The method of claim 26, wherein a rhizobial strain which nodulates said soybean is exposed to a concentration of genistein ranging from about 5 4 µM to about 40 µM.

20. The method of claim 19, wherein said genistein concentration ranges from about 15 µM to about 20 µM.

21. The method of claim 15, wherein said low root zone temperatures are from about 25° C. to about 17° C.

22. The method of claim 19, wherein said low root zone temperatures are from about 17° C. to about 10° C.

23. The method of claim 16, wherein said low root zone temperatures are from about 17° C. to about 10° C.

24. A method for enhancing nodulation of a soybean grown in the field under low root zone temperatures, comprising:
   a) incubating a rhizobial strain which nodulates said soybean with a composition comprising, an agriculturally effective amount of a nodulation gene-inducing compound, in admixture with an agriculturally suitable carrier medium, wherein said effective amount enhances nodulation of said soybean grown in the field under said low root zone temperatures in comparison to an untreated soybean grown under the same conditions; and
   b) inoculating in the vicinity of one of a seed and root of said soybean said rhizobial strain of a), wherein said low root zone temperatures are below 25° C.

25. The method of claim 24, wherein said composition comprises a flavonoid compound.

26. The method of claim 25, wherein said flavonoid compound is selected from the group consisting of genistein and daidzein.

27. The method of claim 26, wherein said rhizobial strain is exposed to a concentration of genistein ranging from about 5 µM to about 40 µM.

28. The method of claim 27, wherein said low root zone temperatures are below about 25° C. to about 17° C.

29. The method of claim 27, wherein said low root zone temperatures are from about 17° C. to about 10° C.

30. The method of claim 24, wherein said low root zone temperatures are from about 17° C. to about 10° C.

31. A method for enhancing protein yield of a soybean grown in the field under low root zone temperatures, comprising,
   a) incubating a rhizobial strain which nodulates said soybean with a composition comprising an agriculturally effective amount of a nodulation gene-inducing compound, in admixture with an agriculturally suitable carrier medium, wherein said effective amount enhances protein yield of said soybean grown in the field under said low root zone temperatures in comparison to an untreated soybean grown under the same conditions, and
   b) inoculating in the vicinity of one of a seed and root of said soybean said rhizobial strain of a), wherein said low root zone temperatures are below 25° C.

32. The method of claim 31, wherein said composition comprises a flavonoid compound.

33. The method of claim 32, wherein said flavonoid compound is selected from the group consisting of genistein and daidzein.

34. The method of claim 33, wherein said rhizobial strain is exposed to a concentration of genistein ranging from about 5 µM to about 40 µM.

35. The method of claim 34, wherein said low root zone temperatures are below about 25° C. to about 17° C.

36. The method of claim 34, wherein said low root zone temperatures are from about 17° C. to about 10° C.

37. A method for enhancing protein yield of a soybean grown in the field under low root zone temperatures, comprising a treatment in the vicinity of one of a seed and root of said soybean with a composition comprising an agriculturally effective amount of a nodulation gene-inducing compound in admixture with an agriculturally suitable carrier medium, wherein said effective amount enhances protein yield of said soybean grown in the field under said low root zone temperatures in comparison to an untreated soybean grown under the same field conditions and wherein said low root zone temperatures are below 25° C.

38. The method of claim 37, wherein said composition comprises a flavonoid compound.

39. The method of claim 38, wherein said flavonoid compound is selected from the group consisting of genistein and daidzein.

40. The method of claim 39, wherein a rhizobial strain which nodulates said soybean is exposed to a concentration of genistein ranging from about 5 $\mu$M to about 40 $\mu$M.

41. The method of claim 40, wherein said low root zone temperatures are below about 25° C. to about 17° C.

42. The method of claim 40, wherein said low root zone temperatures are from about 17° C. to about 10° C.

43. The method of claim 37, wherein said low root zone temperatures are from about 17° C. to about 10° C.

* * * * *